United States Patent
Mellin et al.

(10) Patent No.: US 8,799,009 B2
(45) Date of Patent: Aug. 5, 2014

(54) SYSTEMS, METHODS AND APPARATUSES FOR PREDICTING CAPACITY OF RESOURCES IN AN INSTITUTION

(75) Inventors: Andrew Mellin, Saint Paul, MN (US); Keith Willard, Saint Paul, MN (US); Catherine Whelchel, Spartanburg, SC (US); Mike Myers, Louisville, CO (US); Kristin Oswald, Roseville, MN (US); Michael Altmann, Minneapolis, MN (US)

(73) Assignee: McKesson Financial Holdings, Hamilton (BM)

( * ) Notice: Subject to any disclaimer, the term of this patent is extended or adjusted under 35 U.S.C. 154(b) by 432 days.

(21) Appl. No.: 12/363,954

(22) Filed: Feb. 2, 2009

(65) Prior Publication Data

US 2010/0198609 A1 Aug. 5, 2010

(51) Int. Cl.
*G06Q 50/22* (2012.01)
*G06Q 10/06* (2012.01)
*G06Q 10/00* (2012.01)
*G06F 19/00* (2011.01)

(52) U.S. Cl.
CPC ............... *G06Q 50/22* (2013.01); *G06Q 10/06* (2013.01); *G06Q 10/0639* (2013.01); *G06Q 10/00* (2013.01); *G06Q 10/0637* (2013.01); *G06F 19/327* (2013.01)
USPC ......... 705/2; 705/3; 705/7.38; 703/6; 703/10; 709/204

(58) Field of Classification Search
CPC ... G06Q 50/22; G06Q 10/06; G06Q 10/0639; G06Q 10/00; G06Q 10/0637; G06F 19/327
USPC ..................... 705/2, 3, 7.38; 703/6
See application file for complete search history.

(56) References Cited

U.S. PATENT DOCUMENTS

| | | | | |
|---|---|---|---|---|
| 5,809,477 A | * | 9/1998 | Pollack | 705/3 |
| 7,194,395 B2 | * | 3/2007 | Genovese | 703/6 |
| 7,289,944 B1 | * | 10/2007 | Genovese | 703/10 |
| 7,684,966 B1 | * | 3/2010 | Genovese | 703/6 |
| 8,046,408 B2 | * | 10/2011 | Torabi | 709/204 |
| 8,190,448 B2 | * | 5/2012 | Bajars et al. | 705/2 |
| 8,280,748 B2 | * | 10/2012 | Allen et al. | 705/2 |
| 2003/0074222 A1 | * | 4/2003 | Rosow et al. | 705/2 |
| 2004/0243446 A1 | * | 12/2004 | Wyatt | 705/2 |
| 2005/0137929 A1 | * | 6/2005 | Frazier et al. | 705/9 |
| 2006/0177041 A1 | | 8/2006 | Warner et al. | |
| 2006/0247948 A1 | | 11/2006 | Ellis et al. | |
| 2007/0150307 A1 | | 6/2007 | Lancaster et al. | |
| 2008/0109255 A1 | * | 5/2008 | Allen et al. | 705/2 |
| 2008/0189132 A1 | * | 8/2008 | Minson et al. | 705/2 |
| 2009/0144078 A1 | * | 6/2009 | Bajars et al. | 705/2 |

* cited by examiner

*Primary Examiner* — Dilek B Cobanoglu
(74) *Attorney, Agent, or Firm* — Alston & Bird LLP

(57) ABSTRACT

A method, apparatus, system and computer program product are provided for determining one or more current or future conditions regarding capacity and allocation of resources in an institution. The apparatus enables personnel to utilize predictive tools to identify in real-time or in the near future areas of capacity constraints within the institution. The apparatus includes a processor configured to analyze data which includes information associated with the institution. A portion of the data is generated in real-time during an actual time in which events occur. The processor is capable of using at least a portion of the data to identify current conditions or generate one or more predictions regarding conditions to occur in the future that are associated with resources and capacity of the institution. Also, the processor is capable of analyzing results of the predictions and allocating resources of the institution on the basis of the predicted results.

23 Claims, 10 Drawing Sheets

| Status | Room | Patient Name | | Special Needs | Age | Sex | Diagnosis | Location | Typical DC | Forecast DC | Notes |
|---|---|---|---|---|---|---|---|---|---|---|---|
| IN | 750 | Betty Amples | ⊕ | Alzheimer | 73 | F | MVA, Compou | Telemetry | 03/04/08 1:00p | 03/04/08 1:00pm | 🏠 |
| IN | 752 | Daniel Hasting | | No Known | 30 | M | Right Ankle Re | Neuro ICU | 03/03/08 4:00p | 03/01/08 4:00pm | |
| IN | 760 | Danny Arrago | ⊕ | HOH | 82 | M | Right Total Kne | General Surge | 03/03/08 1:00p | 03/02/08 2:30pm | |
| IN | 762 | Elizabith Murr | | No Known | 41 | F | MVA | DC | 03/05/08 11:00 | 03/04/08 10:00am | |
| IN | 766 | Bob Giltroe | | Codeine Allerg | 54 | M | Total Left Hip | Surgery | 03/03/08 10:00 | 03/03/08 10:00am | |
| IN | 768 | Bob Hailey | | Latex Allergy | 67 | M | Spinal Fusion | Scheduled | 03/06/08 2:00p | 03/04/08 2:00pm | |
| IN | 755 | Greg Martin | ⊕ | No Known | 43 | M | Lumbar Lamino | Surgery | 03/06/08 10:00 | 03/04/08 10:00am | |
| --- | 756 | Predicted | | --- | --- | --- | | | | | |
| OUT | 774 | Patrick Stoll | | Alzheimer | 69 | M | Total Left Hip | Family Pickup | 02/27/08 1:00p | 02/27/08 1:00pm | 🏠 |
| OUT | 757 | Julie Strom | | Penecillin Aller | 57 | F | Spinal Fusion | Family Pickup | 02/27/08 3:30p | 02/27/08 3:30pm | 🏠 |
| OUT | 759 | Dave Stanford | | No Known | 32 | M | Left Ankle Revi | Family Pickup | 02/27/08 10:00 | 02/27/08 10:00am | |

FIG. 6

SYSTEMS, METHODS AND APPARATUSES FOR PREDICTING CAPACITY OF RESOURCES IN AN INSTITUTION

TECHNOLOGICAL FIELD

Embodiments of the invention relate generally to systems, methods, and apparatuses for predicting the capacity of various resources in health care facilities and more particularly relate to providing decision support capabilities to improve resource management and planning.

BACKGROUND OF THE INVENTION

Currently some, health care facilities face problems associated with managing capacity and resources as well as the flow of patients through the health care facility. To complicate matters, over the next twenty years the health care system will likely be confronted with dramatically higher demand on resources and capacity. For instance, as the number of patients entering the health care system increases, the number of health care professionals, such as physicians, nurses, etc. to care for these patients will also likely increase. While the influx of patients in health care environments have not yet hit a critical mass, the impact of these increasing number of patients can be felt within health care facilities, such as hospitals, etc., today.

The capacity and resources of the health care system are affected by a number of variables. For example, baby boomers are steadily reaching an age where more intense health care is needed. There also is an increasing number of emergency room visits due to a declining percentage of the population with health care insurance and Stark law provisions which require access and treatment of patients. Additionally, less than ideal health care facility processes and procedures for ensuring an efficient process of moving patients throughout the facility during their stay as well as inefficient clinical processes for maintaining minimal variations in care between patients impacts the capacity and resources allocated within a health care system.

The above-mentioned problems oftentimes translate into a myriad of negative consequences for health care facilities. In particular, decreased profit margins typically occur as patient lengths of stay increase due to increased care demands and increased complexities in managing care. When capacity loads and patient statuses are not properly predicted, the finite health care resources may be unable to manage current needs in a timely or cost effective manner. Moreover, problems may be manifested as increased patient length of stay or inefficient transfers in level of care where patients unnecessarily spend time in a more expensive unit such as an intensive care unit (ICU) when their condition could be adequately addressed in a less expensive unit. Inefficiencies such as, for example, spending too much time in a health care unit often results in medical care that is not reimbursable by payors, such as insurance companies. Hospitals attempt to address some of the above issues, such as handling an increased influx of patients, by expanding their physical space but typically do so at a cost of about $800,000 per bed. Such costs are frequently impractical, due to the budgetary constraints of health care facilities.

Additionally, increased wait times and other delays may lead to a decrease in patient satisfaction and, in some cases, a decrease in the quality of care provided to patients. Moreover, inappropriately staffed care environments may lead to mistakes in care decisions and higher probabilities of time-dependent care not occurring in the needed window of time which could lead to the patient's health further deteriorating or even worse fatality. For instance, in an emergency room (ED) (also referred to herein as emergency department) in Los Angeles, a woman died of a perforated bowel while in a hospital waiting area. The death was attributed to a delay and breakdown in patient care. Inadequate care, while generally occurring in less dramatic examples, may occur throughout the health care system due to a number of variables such as high congestion (e.g., bottlenecks) in particular unit areas (e.g., Intensive Care Unit) and overcrowding in the health care system, etc.

Furthermore, the unpredictability and turbulence of a hospital care environment with capacity and patient flow difficulties is often detrimental to job satisfaction and retention of skilled staff such as nurses and allied care providers. Increasingly busy health care units and unpredictable patient loads often leaves health care professionals, such as for example, nurses feeling high levels of job stress and decreased abilities to control their work experience. Additionally, long wait times for medical care by patients frequently leads to overworked transport and ancillary staff, which increases employee overtime costs and as noted above may result in an unreimbursed length of stay time for many patients. These variables have been shown to decrease job satisfaction and job retention rates and may result in unsatisfied patients. Moreover, some health care facilities do not have an organized process for ensuring appropriate patient movements through the various units of the health care facility. In this regard, it may be difficult for health care facilities to understand the end-to-end patient flow throughout the enterprise and understand the causes of bottlenecks and backups in the health care system.

Some health care facilities such as hospitals use manual processes such as an all-hands bed huddle or walking the floor and physically counting available beds to garner an understanding of the health care facilities patient flow. Unfortunately, since the bed huddles and walking the floor typically occurs only sporadically, such as once a day, that information quickly becomes inaccurate as the day progresses.

Thus, a need exists to provide an efficient mechanism to predict patient load and capacity for planning and allocating resources in health care facilities and to identify areas of capacity constraints and delays in patient discharges and transfers in real-time as well as in a predictive manner and which will allow information sharing between and within health care units of a health care facility.

BRIEF SUMMARY OF THE INVENTION

Exemplary embodiments of the invention provide a mechanism in which devices may utilize one or more predictive tools that incorporate flow between health care units, staffing, and clinical information to allow health care organizations to identify in real-time or in the near future, areas of capacity constraints, flow problems, supply (e.g., number of appropriate nurses/doctors, etc.) and demand (e.g., number of current patient) mismatches. These tools provide real-time and future visibility of capacity problems and identify delays in patient discharges and transfers as well as synchronization of schedules (e.g., staffing schedules) across health care units. There is a need to provide functionality that will allow for sharing between and within units of real time patient information, predicted bed capacity, and ad hoc communications. By identifying and highlighting patients available for transfer or discharge, clinicians will be better situated to discharge patients in a time-appropriate manner.

Additionally, exemplary embodiments of the invention are capable of anticipating and determining bed capacity which allows for streamlined bed planning and increased efficiencies in improving the room turnaround process so that new patients and/or existing patients may utilize these rooms. In this regard, the exemplary embodiments of the present invention foster utilization of efficient health care bed capacity and throughput to thereby minimize costs associated with adding more beds, which can cost over $800,000 per bed. Moreover, exemplary embodiments of the invention provide an organized process for ensuring appropriate movements of patients through the various health care units (e.g., operating room, intensive care unit, etc.) of a health care facility such as for example a hospital and are capable of identifying an efficient end-to-end patient flow through the health care facility as well as the cause of bottlenecks and backups and other inefficient flow patterns.

In addition, exemplary embodiments of the invention provide real-time and future visibility of capacity problems and delays in patient discharges and transfers and improves patient throughput within the health care facility. Furthermore, the exemplary embodiments of the invention are capable of utilizing tools to efficiently predict staff schedules so that staff management does not have to guess as to future personnel needs. In this regard, the exemplary embodiments of the present invention provide a mechanism for anticipating staff needs based on demand, which is beneficial since one of the top factors for throughput, quality, and safety is that the appropriate personnel with the right skill set mix be available during a patient's stay at the right time. To increase throughput, patient safety, and employee morale, the exemplary embodiments of the invention may provide modeling and predictive capabilities for both medium term (e.g., 4 to 8 weeks) and short-term (e.g., 3 to 72 hours) patient stays.

Exemplary embodiments of the invention also serve to decrease ancillary wait times of patients for inpatient tests and procedures relative to those experienced in existing health care facilities and which sometimes contribute to unit-level bottlenecks and extended lengths of stay and may result in overworked transport and ancillary staff, which may increase employee overtime costs, increased turnover rate in employment and unreimbursed lengths of stay time for patients. In this regard, the exemplary embodiments of the present invention predict patient loads, staff schedules, and provide visibility into transport processes which lead to increased capacity efficiencies.

Exemplary embodiments are capable of determining or predicting when units (e.g., health care units) will be at or near capacity in the future. Additionally, the exemplary embodiments are capable of determining or predicting where bottlenecks in patient flow between units may occur in the future and how to best match staffing needs for a unit(s) to optimize flow and capacity within a health care facility in the future.

In one exemplary embodiment, a corresponding method and computer program product are provided. The method and computer program product may include analyzing data, including information associated with an entity such as a facility. At least some of the data is generated in real-time during an actual time in which one or more events may occur. The method and computer program product may use at least a portion of the data to generate one or more predictions regarding one or more conditions to occur in the future that are associated with resources of the entity and analyze one or more results of the predictions and recommend an allocation of resources of the entity on the basis of the results. The method and computer program product may also determine that one of the conditions corresponds to identifying a number of beds or rooms in a unit(s) of the entity that will be available at a predetermined time in the future. Additionally, the method and computer program product may determine that another condition corresponds to one or more levels of congestion within a unit(s) of the entity. The congestion corresponds to a number of individuals assigned to a respective unit.

In yet another exemplary embodiment, an apparatus is provided for determining one or more current conditions and predicting one or more future conditions associated with capacity and resources of an entity. The apparatus includes a processor configured to analyze data, including information associated with an entity. The entity may be a facility such as a health care facility. At least some of the data is generated in real-time during an actual time in which one or more events may occur. The processor is further configured to use at least a portion of the data to generate one or more predictions regarding one or more conditions to occur in the future that are associated with one or more resources of the entity and analyze one or more results of the predictions and recommend an allocation of at least one of the resources on the basis of the results. The processor is further configured to determine that one of the conditions corresponds to identifying a number of beds or rooms in a unit(s) of the entity that will be available at a predetermined time in the future. The processor is also configured to determine that another condition corresponds to one or more levels of congestion within a unit(s) of the entity. The congestion corresponds to a number of individuals assigned to a respective unit.

BRIEF DESCRIPTION OF THE SEVERAL VIEWS OF THE DRAWINGS

Figure 1:
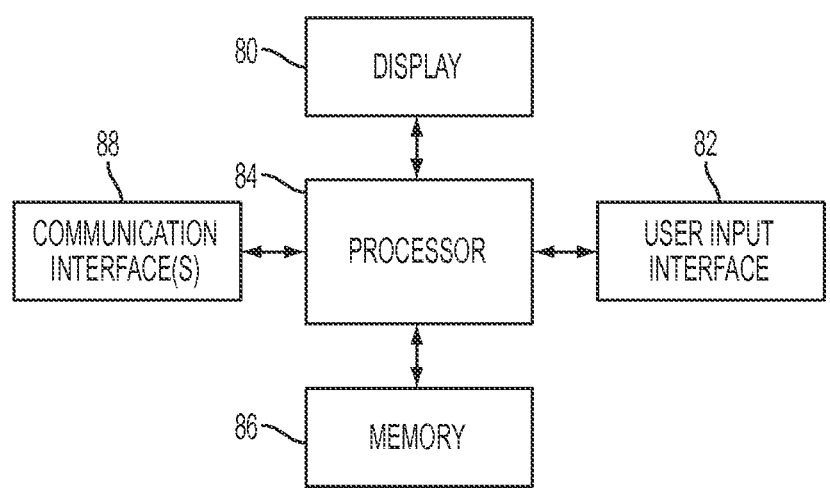
Figure 2:
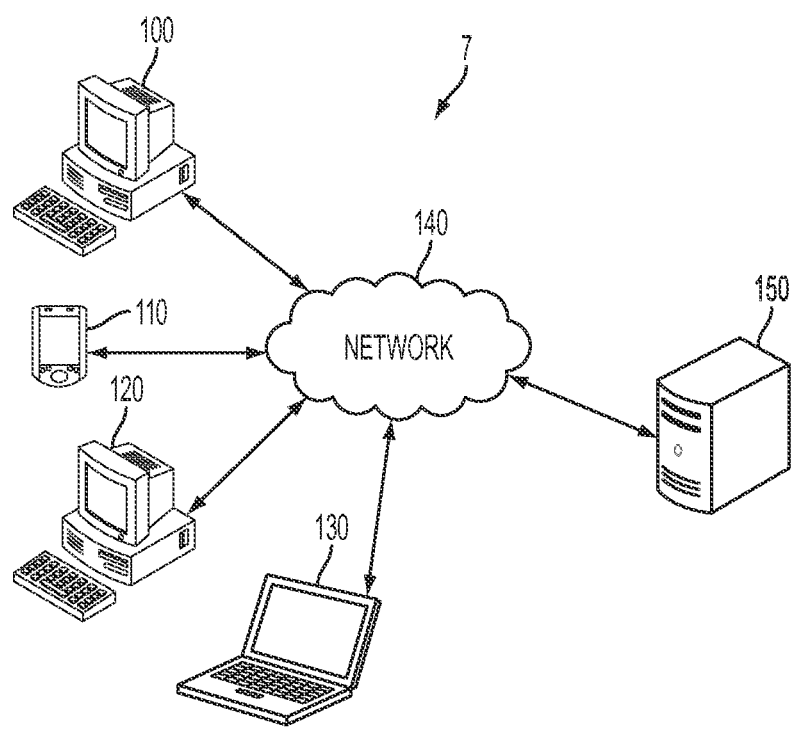
Figure 3:
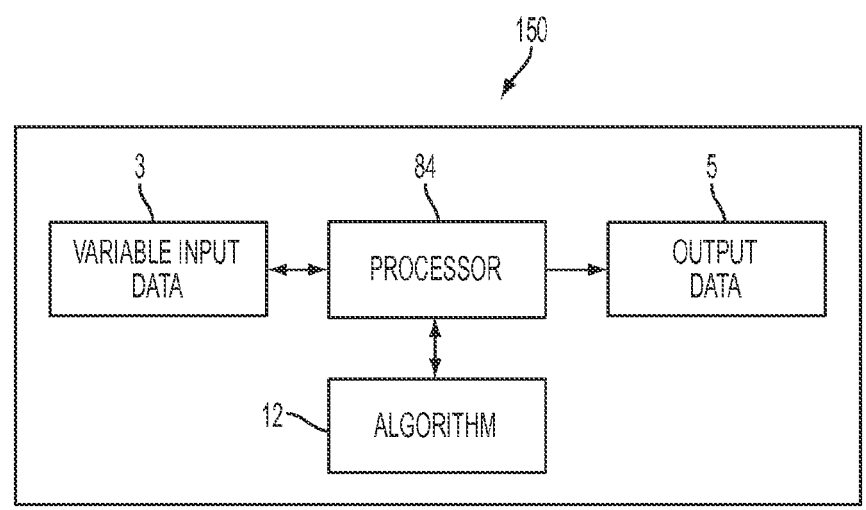
Figure 4:
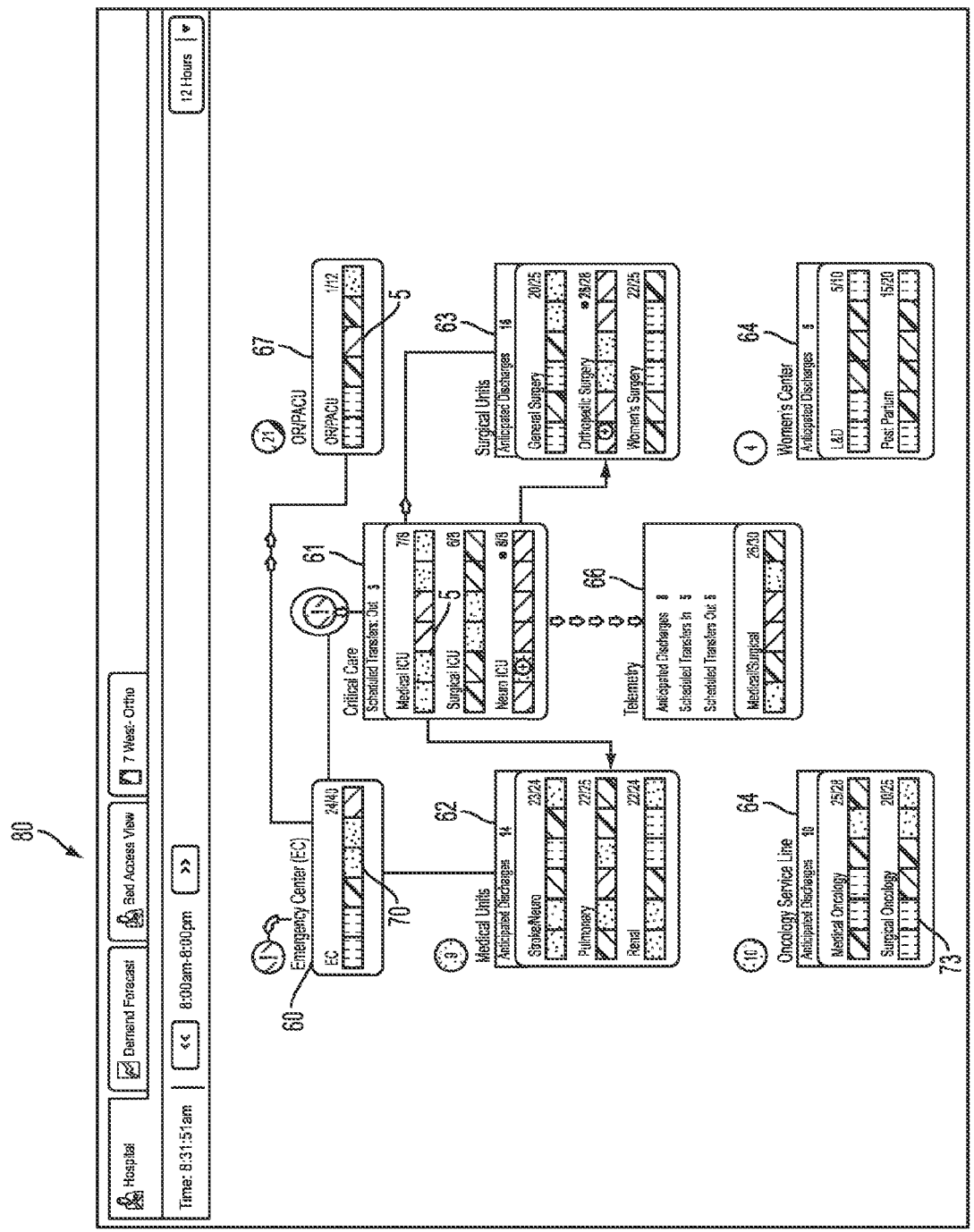
Figure 5:
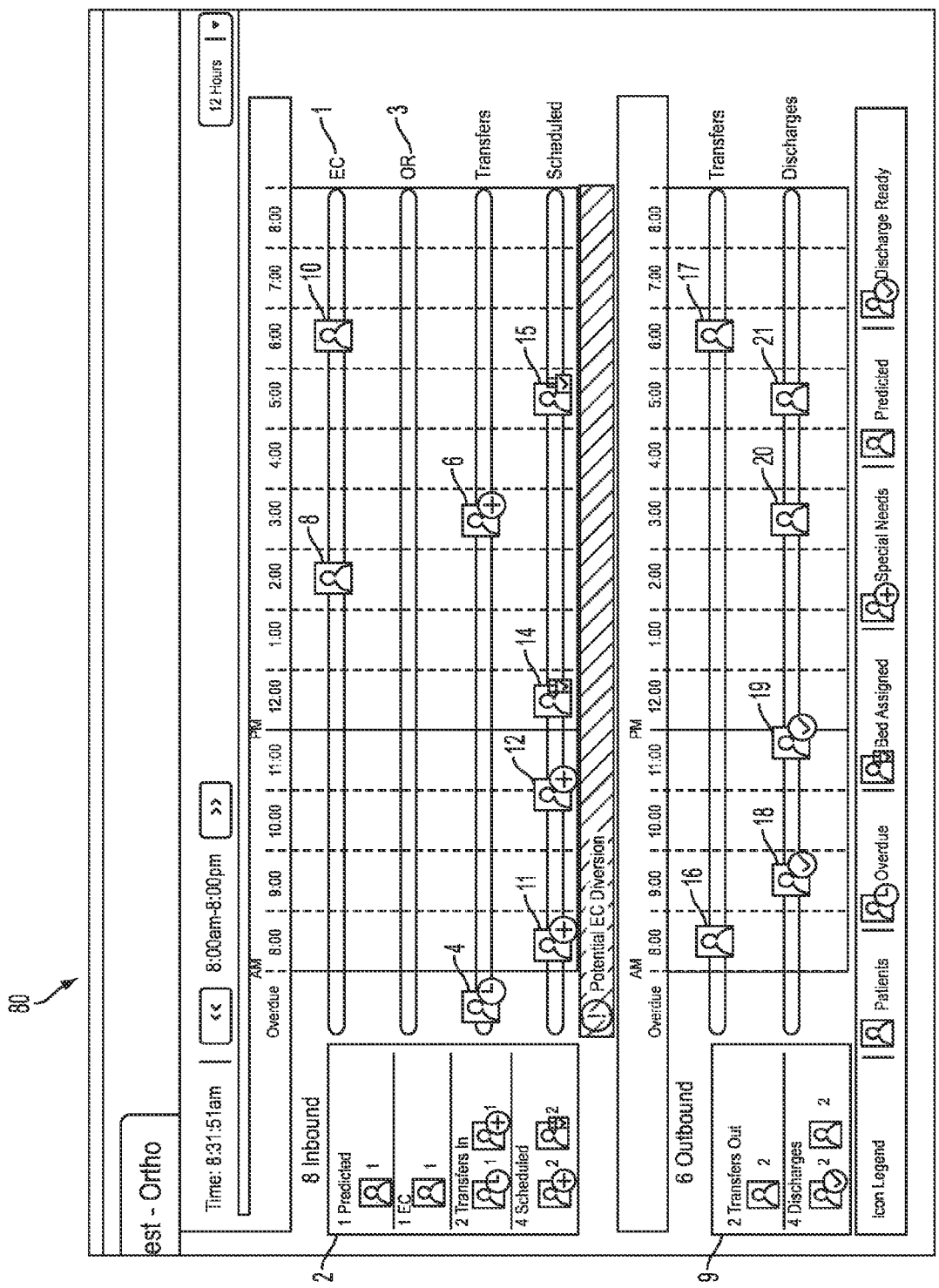
Figure 7:
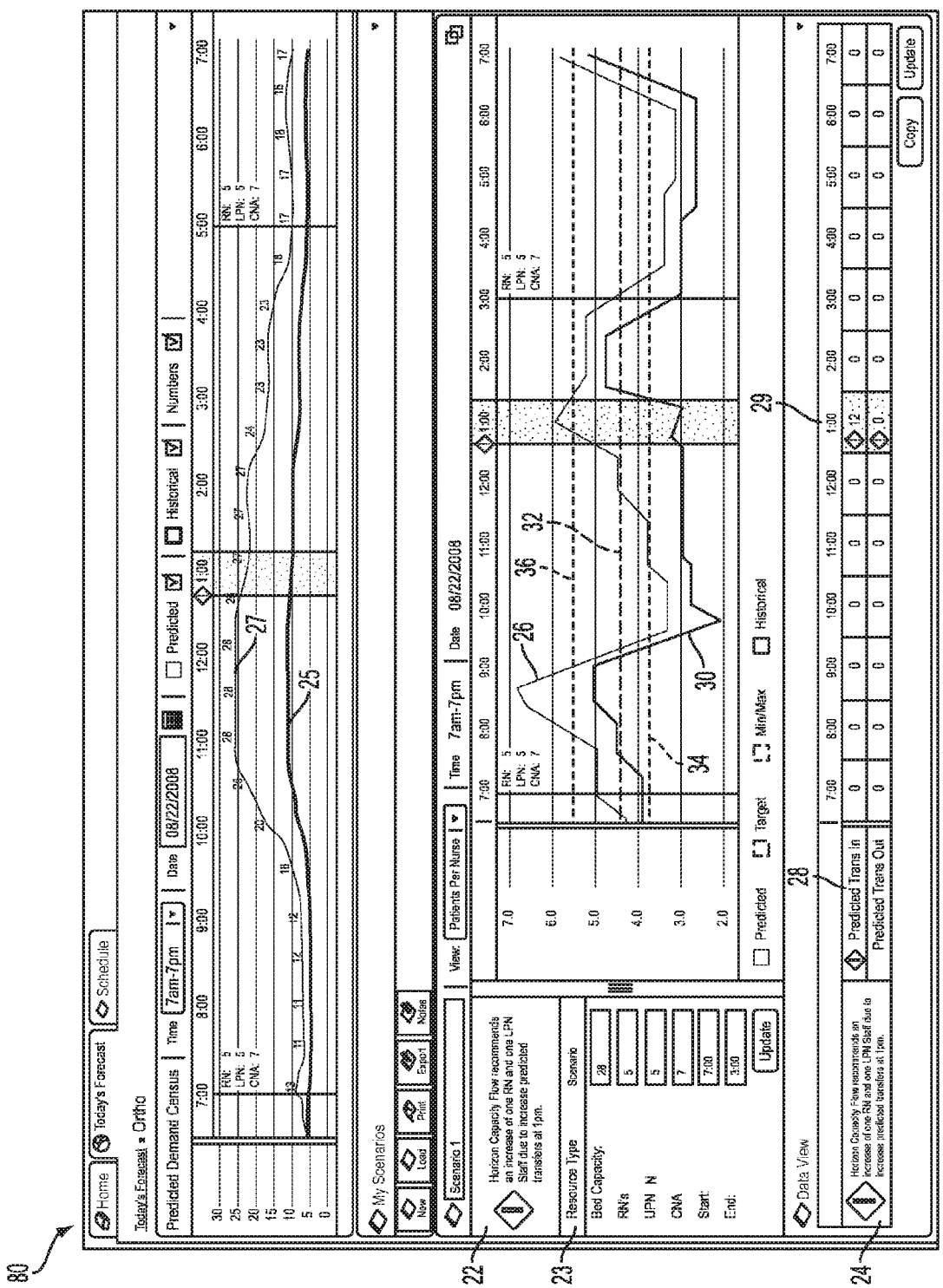
Figure 8:
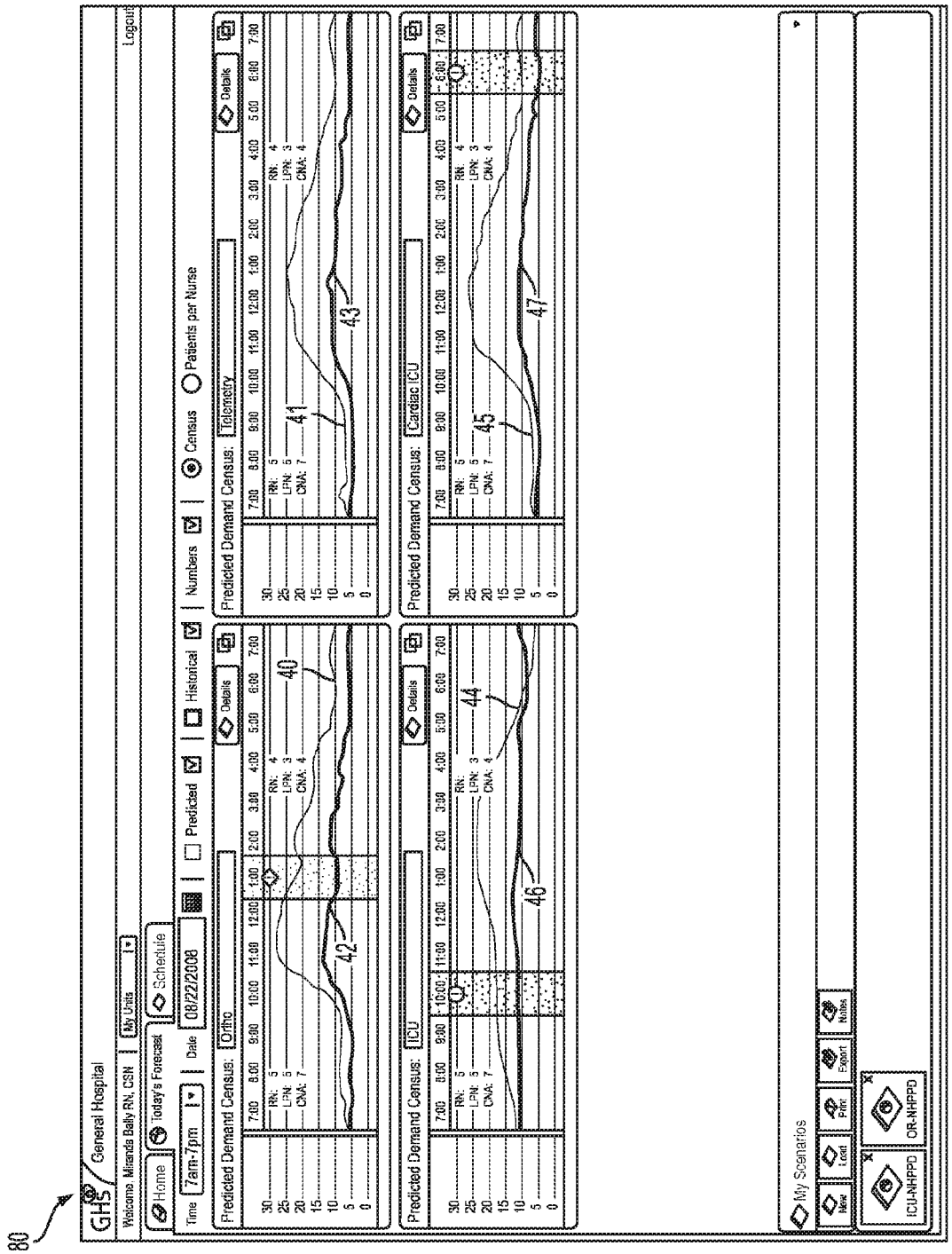
Figure 9:
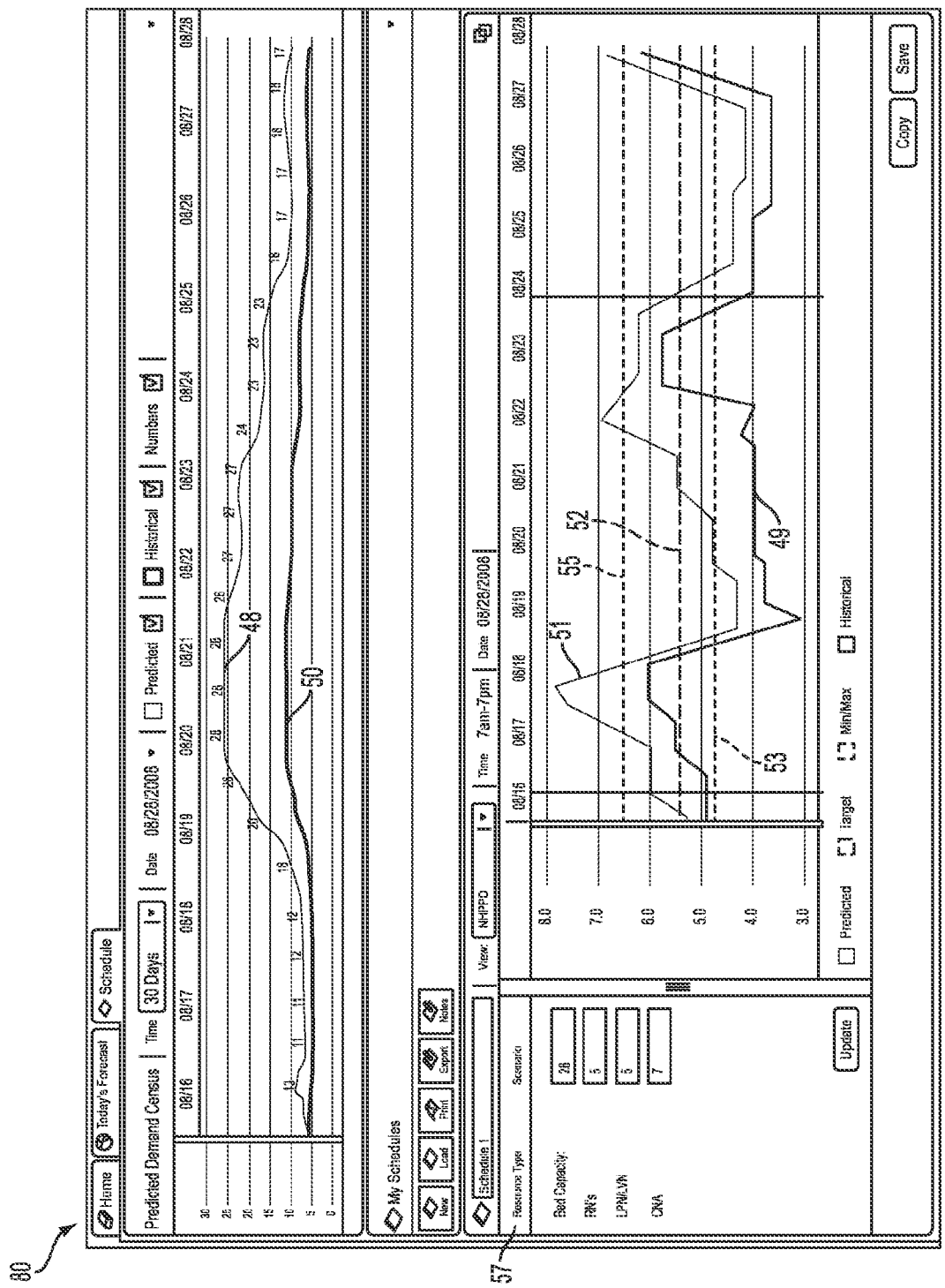
Figure 10:
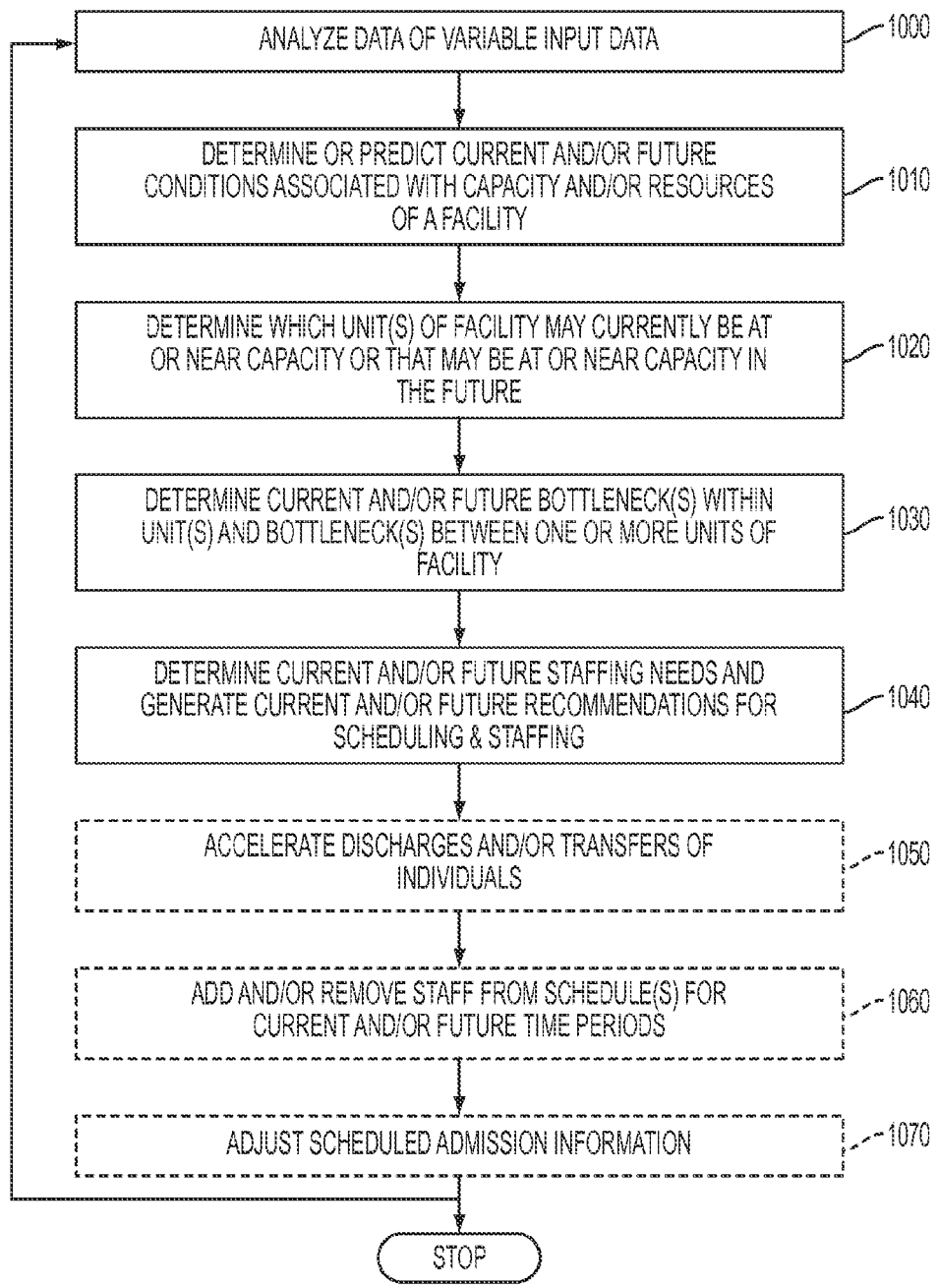

Having thus described the invention in general terms, reference will now be made to the accompanying drawings, which are not necessarily drawn to scale, and wherein:

FIG. 1 is a schematic block diagram of an electronic device according to an exemplary embodiment of the invention;

FIG. 2 is a schematic block diagram of a system according to an exemplary embodiment of the invention;

FIG. 3 illustrates a schematic block diagram of an entity capable of determining current and/or future conditions regarding capacity and allocation of resources in a facility or institution according to an exemplary embodiment of the invention;

FIG. 4 illustrates a display showing one or more bottlenecks or choke points in a medical institution according to an exemplary embodiment of the invention;

FIG. 5 illustrates a display showing scheduled and predicted patient flow within a unit(s) of a medical institution according to an exemplary embodiment of the invention;

FIG. 6 illustrates a display showing medical information associated with one or more patients according to an exemplary embodiment of the invention;

FIG. 7 illustrates a display showing one or more short term predictions associated with medical personnel of a medical institution according to an exemplary embodiment of the invention;

FIG. 8 illustrates a display showing one or more medium term predictions associated with medical personnel of a medical institution according to an exemplary embodiment of the invention;

FIG. 9 illustrates one or predictions associated with scheduling medical staff personnel according to an exemplary embodiment; and FIG. 10 illustrates a flowchart for utilizing variable input data to determine one or more current and/or future conditions regarding capacity and/or resources in a facility or institution according to an exemplary embodiment of the invention.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

FIG. 1 illustrates a block diagram of an electronic device such as a client, server, computing device (e.g., personal computer (PC), computer workstation, laptop computer, personal digital assistant, etc.) or the like that could implement embodiments of the invention. The electronic device includes various means for performing one or more functions in accordance with exemplary embodiments of the invention, including those more particularly shown and described herein. It should be understood, however, the electronic device(s) of the exemplary embodiments may include alternative means for performing one or more like functions, without departing from the spirit and scope of the invention. More particularly, for example, as shown in FIG. 1, the electronic device can include a processor 84 connected to a memory 86. The memory can comprise volatile and/or non-volatile memory, and typically stores content, data or the like. For example, the memory may store content transmitted from, and/or received by, the electronic device. The memory 86 is capable of storing data including but not limited to information related to a unit(s) of a facility or institution (e.g., emergency department (ED) or emergency room (ED) information of a health care facility (e.g., hospital), current and past inpatient census information, current and past surgery and admission schedules, current and past admission, admission discharge transfer (ADT) information, information relating to a capacity of organization, such as for example, bed/room capacity information of a health care facility, flows of an organization(s), staffing information, clinical information, (e.g., patient acuity data, one or more physician orders, etc.) individual patient data and any other suitable data. This data that may be stored in memory 86 and may be referred to herein as variable input data since the data may be changed and updated in real-time.

Also for example, the memory typically stores client applications, instructions or the like for execution by the processor 84 to perform steps associated with operation of the electronic device in accordance with embodiments of the present invention. As explained below, for example, the memory can store one or more client application(s) such as for example software or algorithms associated with identifying current and future capacity and allocation of resources within an organization or institution, such as for example a health care facility which provides decision support capabilities to the organization. In this regard, the software may improve patient throughput within a health care system and enhance resource planning in the health care system.

The electronic device can include one or more logic elements for performing various functions of one or more client application(s). The logic elements performing the functions of one or more client applications can be embodied in an integrated circuit assembly including one or more integrated circuits integral or otherwise in communication with a respective network entity (i.e., computing system, client, server, etc.) or more particularly, for example, a processor 84 of the respective network entity.

In addition to the memory 86, the processor 84 can also be connected to at least one interface or other means for displaying, transmitting and/or receiving data, content or the like. The interface(s) can include at least one communication interface 88 or other means for transmitting and/or receiving data, content or the like. In this regard, the communication interface 88 may include, for example, an antenna and supporting hardware and/or software for enabling communications with a wireless communication network. For example, the communication interface(s) can include a first communication interface for connecting to a first network, and a second communication interface for connecting to a second network. In this regard, the electronic device is capable of communicating with other electronic devices over a network such as a Local Area Network (LAN), Wide Area Network (WAN), Wireless Wide Area Network (WWAN), the Internet, or the like. Alternatively, the communication interface can support a wired connection with the respective network. In addition to the communication interface(s), the interface(s) can also include at least one user interface that can include one or more earphones and/or speakers, a display 80, and/or a user input interface 82 (also referred to herein as a graphical user interface (GUI)). The display 80 is capable of displaying information including but not limited to adaptive predictions associated with patient care, information associated with patient flow throughout various units (e.g., operating room (OR), ICU, ED, etc.) of a health care facility (e.g., a hospital), high congestion units/areas (also referred to herein as bottlenecks and/or choke points) within a health care facility, and model and/or predictive staffing changes as well as any impact on medical care capacity. The user input interface, in turn, can comprise any of a number of devices allowing the entity to receive data from a user, such as a microphone, a keypad, keyboard, a touch display, a joystick, image capture device, pointing device (e.g., mouse), stylus or other input device.

Reference is now made to FIG. 2, which is a block diagram of an overall system that would benefit from exemplary embodiments of the invention. It should be pointed out that one or more of the components of FIG. 2 may comprise the elements of the electronic device illustrated in FIG. 1. As shown, the system 7 may include one or more electronic devices 100, 110, 120, 130 (e.g., personal computers, laptops, personal digital assistants and the like) which may be operated by medical personnel (e.g., nurses, physicians, etc.) on behalf of one or more health care facilities/institutions (e.g., hospitals, clinics, etc.) or the like in order to access a server 150, or similar network entity, over a network 140, such as a wired or wireless local area network (LAN), a metropolitan network (MAN) and/or a wide area network (WAN) (e.g., the Internet). Although four electronic devices 100, 110, 120 and 130 are shown in FIG. 2, it should be pointed out that any suitable number of electronic devices may be part of the system of FIG. 2. Each of the electronic devices may be operated by a particular unit(s) (e.g., health care unit(s)) of an institution such as a health care facility (e.g., hospital).

The server 150 may retrieve some or all of the variable input data from its memory 86. In this regard, some or all of the variable input data may be saved to the memory 86 using the user input interface 82 of the server 150. Additionally or alternatively, the processor 84 of the server 150 may receive some or all of the variable input data from any of the electronic devices 100, 110, 120 and 130 which then may be stored by the processor 84 in the memory 86. As described above, some of the variable input data consists of Admission Discharge Transfer (ADT) data. The ADT data may include but is not limited to data related to the management of patient admission(s) to a facility or institution (e.g., health care facility), discharges, room/bed assignments, transfers between units (e.g., health care units and/or health care facilities), census information relating to a total number of patients in a facility or institution and any other suitable data. In this regard, the processor of the server 150 may utilize the communication interface 88 to send the ADT data to the electronic devices 100, 110, 120, 130 and 150. Additionally, the processor of the server 150 may analyze the ADT data and generate one or more census reports, which may be stored in its memory, and which may be sent to one or more of the electronic devices 100, 110, 120 and 150 which may be operated by a particular unit(s) (e.g., health care unit(s)) and be accessible to staff personnel such as for example medical staff personnel including but not limited to nurses, physicians, financial coordinators, managers and the like.

Upon being admitted to a facility or institution (e.g., health care facility such as for example a hospital), information associated with the admission may become part of the ADT data and staff personnel (e.g., health care staff) may utilize the server 150 to analyze the ADT data to determine whether there is room/bed availability and if so, the processor of the server may automatically assign a resident(s) (e.g., patient) a room/bed. In this regard, the processor of the server is able to access the entire room/bed inventory of a facility or institution upon a person being admitted in order to identify the proper accommodations for each person. The processor of the server may send information to each of the electronic devices 100, 110, 120, and 130 providing predictive recommendations around the assignment of rooms and/or beds of a facility (e.g., health care facility) to individuals (e.g., patients). Additionally, the processor of the server 150 may predict from the census information when there is no more room and/or bed availability within the facility. Alternatively, the processor 84 of the server may also predict when the room and/or bed availability of the facility will be near capacity when the processor 84 of the server 150 determines that the number of rooms and/or beds that are available (e.g., unoccupied rooms and/or beds) is below a predetermined threshold (e.g., 30 rooms and/or beds) or below a predetermined percentage of available rooms/beds (e.g., 10%).

It should be pointed out that the memory 86 of the server 150 is also capable of storing a person's clinical, bibliographic and demographic data, as well as the person's entire medical treatment history including but not limited to attending doctors, procedures, diagnoses and medications, which may be used by staff personnel to make informed decisions for future care and for predicting or determining appropriate resources necessary for providing the appropriate level of care to one or more patients. Additionally, the memory 86 may store any other suitable information, data content or the like.

As described above, the ADT data includes but is not limited to information relating to resident (e.g., patient) admissions, discharges, room/bed assignments, transfers, census information, individual patient clinical data and the like. In exemplary embodiments, the processor of the server 150 may utilize one or more electronic data feeds, one or more Health Level Seven (HL7) healthcare standard interfaces, Electronic Data Interchange (EDI), one or more data stores or any other suitable mechanisms, to analyze information and determine that the information should be designated or categorized as ADT data. In an exemplary embodiment, it should be pointed out that one type of HL7 protocol referred to as an "ADT" protocol may be utilized to analyze the information and determine that the information should be designated or categorized as ADT data. Additionally, in an alternative exemplary embodiment, one type of HL7 protocol referred to as Scheduling Information Unsolicited (SIU) messages may be utilized. The SIU messages may be used to communicate information about a patient's appointment from a hospital scheduling system to a physician or clinic's practice management system. SIU messages are a part of the HL7 Standard. Additionally, the SIU messages may be used for transmitting scheduling information and may also be used to analyze information and determine whether the information should be designate as ADT data. For example, when information including but not limited to admission, discharge, transfer, census data, or room/bed capacity is received by the processor of the server 150 via the communication interface 88 or the user input interface 82, for example, the processor of the server is able to designate or categorize this information as ADT data. Alternatively or additionally, a person using the user input interface 82 of the server 150 may categorize and designate the information as ADT data. The information designated/categorized as ADT data may be stored in the memory of the server.

It should be pointed out that the processor 84 of the server 150 is capable of accessing and analyzing the ADT data in real-time. Some or all of the ADT data may be received by the processor 84 of the server 150, via the communication interface 88, from one or more of the electronic devices 100, 110, 120 and 130. Additionally or alternatively, some or all of the ADT data may be received by the processor of the server 150 when the ADT data is input by a person (e.g., a medical staff member) utilizing for example a keyboard or the like of the user input interface 82. For example, medical personnel may utilize the keyboard of the user input interface 82 of the server 150 to specify that a person would like to be admitted to a facility (e.g., health care facility such as a hospital). Once the person's admission information, or any other suitable ADT data (e.g., a request to transfer to another facility), is provided to the processor of the server 150 via the user input interface 82 and/or the communication interface 88, the processor of the server 150 is capable of analyzing this ADT data in real-time, i.e., the actual time during which an event or condition occurs. For instance, in the example above, the processor of the server 150 may analyze the admission information during the time that the patient is actually seeking admission to the facility and in which the admission information is being generated by a member of the medical staff utilizing the user input interface. In this regard, the processor 84 of the server 150 is capable of analyzing the ADT data in real time as it is received by the processor 84.

The processor of the server 150 is also capable of accessing and analyzing data associated with one or more schedules. Data associated with the schedules may be received from any of the electronic devices 100, 110, 120 and 130 or by a user utilizing the user input interface 82 of the server. Information associated with the schedules may include but is not limited to data associated with work times of personnel (e.g., nurses, lab technicians, etc), the number of personnel available to work any given day of a week, etc. The information associated with schedules may also relate to one or more units (e.g., health care units such e.g., OR, ED, ICU, etc.) of a facility and any other suitable information. In this regard, the schedules may consist of data specifying the time in which medical diagnoses, examinations or procedures, etc. are designated to be performed within the unit. For purposes of illustration and not of limitation, a schedule(s) may include data specifying the operating times for the operating room unit. The processor may access information in real-time. The processor of the server 150 is capable of analyzing data that is input to any of the schedules in real time, i.e., as the processor receives the information.

Additionally, the processor of the server 150 is able to analyze and detect any changes made to the schedules in real-time as these changes are input to the schedules, for example by a user utilizing the user input interface 82. For instance, a change in a schedule may invoke the processor of the server to analyze the data in the respective schedule to identify the schedule change(s). The processor of the server 150 may send updated schedule information to any of the electronic devices 100, 110, 120 and 130 which may be accessible by personnel of a facility (e.g., hospital).

The processor 84 of the server 150 is also capable of analyzing historical data and patterns, and any other suitable data, associated with a facility or institution (e.g., health care facility) to formulate predictions and generate forecasts regarding the capacity and recourses of a facility or institution such as, for example, a health care institution (e.g., hospital). The historical data may be stored in memory 86 of the server 150. In this regard, the processor of the server 150 may examine historical data including but not limited to data associated with the average number of patients admitted to a health care facility for a given time period e.g., day of the week, the average number of patients admitted during a given week of the year (e.g., Week 1), the average number of patients admitted during a given season of the year (e.g., summer, Thanksgiving holiday season, etc.). The processor of the server 150 may also analyze historical patterns associated with the average number and type of personnel (e.g., nurses, doctors, administrators, etc.) that work during a given time for example a day of the week, week of a year, month, season (e.g., quarterly), and year as well as other suitable information. For instance, the processor of the server 150 may determine that on average 100 nurses typically work in December but in February only 70 nurses typically work on average.

The processor 84 of the server 150 may also examine historical data associated with units of a facility such as for example health care units of a hospital. For purposes of illustration and not of limitation, the processor of the server 150 may analyze historical data patterns and identify the average number of patients admitted to a unit (e.g., ED unit) during a given time (e.g., during a day, month, year, season, etc., the number/type of medical conditions treated, the number/type of medical examinations and surgeries or medical operations that were performed based on an admitted number of patients and any other suitable information.

Moreover, as discussed more fully below with respect to FIG. 3, the processor of the server 150 may execute an algorithm and examine variable input data such as for example, ADT data (or any other variable input data) and perform a prediction on the basis of the ADT data. For example, the processor of the server 150 may analyze the ADT data and determine that there is a predetermined number (e.g., 25) of patient transfers and/or discharges for an upcoming day on the basis of the ADT information. In this regard, the processor 150 of the server may predict a number of medical staff personnel needed for a given time of day, day of a week or week of a year, etc. It should be pointed out that predictions for a given time of day, day of week, week of year, month of year or any other successive interval of time may be referred to herein as time series predictions. Additionally, by evaluating the ADT information, the processor of the server may also generate one or more short term predictions. For purposes of illustration and not of limitation, the processor of the server 150 may analyze the ADT data and/or other patient information and identify a number of patient transfers that are to occur for a given time period in the immediate or near future and the processor of the server 150 may determine on the basis of the ADT information that there is only room/bed availability to transfer patients between two units (e.g., ED and OR) of a health care facility (e.g., hospital) within the next 24 hours. In an exemplary embodiment, a short term prediction may be a prediction valid for a window of time between 0 and 72 hours. However, it should be understood that the short term prediction may be valid for any suitable time period without departing from the spirit and scope of the invention.

Referring now to FIG. 3, a processor of a server is shown which is capable of receiving variable input data and executing an algorithm which generates forecasts and predictions regarding capacity and resources of a facility or institution. As can be seen in FIG. 3 and as described above, the processor 84 of the server 150 is configured to analyze variable input data including but not limited to a unit(s) (e.g., emergency department (ED) information or emergency room (ED) information of a health care facility) of a facility or institution (e.g., health care facility e.g., a hospital), current and past inpatient census information, current and past surgery and admission schedules, current and past admission data, ADT information, information relating to a capacity of an organization, such as for example, bed/room capacity information of a facility (e.g., health care facility), flows of an organization(s), staffing information, clinical information (e.g., one or more orders (e.g., physician and/or pharmacy orders, etc.), acuity information, etc.), individual patient data and any other suitable data. It should be pointed out that the variable input data may be in the form of HL7 data and while analyzing the variable input data, the processor 84 may parse some or all of the variable input data which may be used by the algorithm when executed by the processor. Using the variable input data 3, the processor of the server 150 may execute the algorithm 12 and generate one or more predictions or forecasts as well as output data 5 which may be sent to any of the electronic devices 100, 110, 120, and 130 via the communication interface(s) or may be displayed by display 80. The algorithm 12 may consist of one or more computer readable instructions and may be in the form of software. The variable input data may be modified or updated at any given time. It should be pointed out that while FIG. 3 shows that the processor 84 of the server 150 may execute algorithm 12 that the processor of the server 150 may execute any number of algorithms. For instance, in an alternative exemplary embodiment, the algorithm 12, may be used to predict short term patient flow and another algorithm may be used to predict longer term staffing needs.

The processor of the server 150 is able to execute an algorithm 12 which identifies units that may be at or near capacity in the future (e.g., between 0 and 72 hrs. or any other suitable time in the future). Additionally, the processor 84 of the server 150 is able to execute the algorithm to determine whether there may be bottlenecks or choke points within a unit and between units of a facility in the future and determine how to best match the staffing needs of one or more units to optimize flow and capacity within a facility in the future as described more fully below.

In this regard, the algorithm 12 may utilize one or more statistical techniques for generating forecasts and predictions regarding capacity and allocation of resources of a facility. The statistical technique(s) may consist of time series auto-regression techniques, for example Box-Jenkins statistical and forecast techniques. The time series auto-regression technique may be used to make forecasts or generate predictions for medium term (e.g. 4 to 6 weeks) or longer. In another alternative exemplary embodiment, long term forecasts and predictions may be generated for a time period of 6 months or more from a current date whereas short and medium term forecasts and predictions may be for a time period of 6 months or less. For short term forecasts in the range of 1-72 hours the algorithm 12 may utilize a stochastic differential equation model consisting of parameters associated with patient movement.

The algorithm 12 may generate current and/or future staffing recommendations on the basis of a derivation from a first-order autoregression model consisting of parameters associated with one or more work shifts of staff. The first-order autoregression model is as follows:

$$C[i]=S[\text{shift}(i)]+D[\text{day}(i)]+M[\text{month}(i)]+\text{alpha} X\ C[i-1]+\text{epsilon}[i],$$

where $C[i]$ denotes the census as the ith timer period or department of a facility during an ith shift, $S[j]$ denotes the effect of the jth shift of the day, $D[j]$ denotes the effect of the jth day of the week, $M[j]$ denotes the effect of the jth month of the year, and alpha measures the tendency for one shift to be like the next, and epsilon[i] denotes independently and identically distributed residual errors.

It should be pointed out that the algorithm 12 may determine average individual (e.g., patient) throughput within a facility based on a derivation from an autoregression model consisting of parameters associated with patient movement. The information derived from the autoregression equation model may be used for short term (e.g., the next 0 to 72 hours) predictions for instance for estimating forecasts of patients, staff (e.g., nurses, doctors), etc. moving between units (e.g., moving from ED to OR, ICU, general ward, etc. For example, the statistical model for the census in the Orthopedics unit on a Tuesday afternoon shift in July may correspond to the following:

$$C[i]=0.5+1.2-0.6+0.84*C[i-1]+\text{epsilon}$$

Where 0.5 indicates that the afternoon shift census is typically 0.5 patients higher than the average for all shifts, 1.2 reflects the that Tuesdays are typically 1.2 patients higher than the average for all days, −0.6 reflects the fact that July censuses are typically 0.6 patients lower than average, 0.84 indicates the correlation between the census at the morning shift and the census at the afternoon shift, and epsilon represents the residual error.

Suppose that the census in the morning shift was 30, then the algorithm 12 employing the statistical model may predict that the afternoon shift would be 26. Supposing further that the staffing ratios for registered nurses (RNs) and licensed practical nurses (LPNs) was 4:1 and 3:1, then the model would predict that the hospital would need 7 RNs and 9 LPNs for the Tuesday afternoon shift.

One use of the autoregression model is to predict the flow from the ED into the ICU based on applying the autoregression model to the ED and then using information concerning the time spent in the ED and the fraction of ED patients who are transferred to the ICU. The algorithm 12 may also utilize a micro-population Monte Carlo simulation model in which individuals (e.g., patients), beds/rooms and staff personnel may be modeled and transition probabilities may be estimated from current historical data of the variable input data in order to determine various forecasts and predictions associated capacity and resources of a facility relating to volume of patients within a facility and units within the facility, capacity of beds/rooms of a facility, staff or personnel needs, schedule changes and identification of bottlenecks within and between units of a facility. By utilizing known information, such as for example, known historical trends, current patient admissions and transfers upstream to a given ward, as well as certain key patient specific data such as admitting diagnosis or some relevant clinical information, the processor of the server 150 may execute the algorithm 12 and predict for a given ward which patients are more likely to leave the ward or be admitted to the ward. This refined estimate of patient flow can be coupled to staffing load predictions to forecast future staffing load requirements for specific wards. The algorithm 12 may be executed by the processor of the server to forecast a particular patient's progression through the hospital and may use information corresponding to the patient's age, gender, admitting diagnosis, admitting department and the specialty of the admitting physician. In an alternative exemplary embodiment, the algorithm 12 may utilize natural language processing to map free-text admitting diagnosis to an (International Classification of Diseases) ICD-9 code. The ICD-9 code provides codes to classify diseases and a wide variety of signs, symptoms, abnormal findings, complaints, social circumstances and external causes of injury or disease. Every health condition can be assigned to a unique category and given a code, up to six characters long. The "9" in ICD-9 refers to the $9^{th}$ edition of the list which was extended to capture more morbidity data and added procedure codes. Additionally, the ICD-9 code may then utilize available maps from ICD-9 to Hierarchical Condition Category (HCC) or to Diagnosis related group (DRG) to group patients. The Hierarchical Condition Category is a risk adjustment model for all inpatient and outpatient encounters based on disease grouping and the Diagnosis related group (DRG) is a system to classify hospital cases into one of approximately 500 groups expected to have similar hospital resource use. In another alternative exemplary embodiment, the algorithm 12 may be utilized to train a neural network to predict LOS (e.g., either directly or via DRG) based on information obtained from one or more admitting diagnosis, an admitting department and/or a specialty of an admitting physician.

The processor of the server 150 is also capable of executing the algorithm to estimate and predict a number of individuals (e.g., patients, medical staff, etc.) that require schedule changes with respect to a unit(s) such as a health care unit for example. Schedule changes are oftentimes required when one or more patients cancel a scheduled operation to be conducted by a physician in the operating room, when patients do not show up at their scheduled time or when the velocity of patients moving through units is highly variable such as patients moving through the OR and post anesthesia care unit (PACU) which may ultimately affect scheduling or for any other suitable reasons. Additionally, health care staff such as nurses and physicians work schedules often changes for personal reasons, due to patient cancellations or a number of other reasons. In this regard, the algorithm may use a mixture of deterministic information and stochastic elements to predict the type of patient(s), procedure(s), health care staff members, etc. that are frequently involved in schedule changes and may automatically generate alternative scheduling arrangements. It should be pointed out that part of the patient flow (which includes, but is not limited to staffing load information) may be known more or less deterministically due to the scheduling systems. For example, patients may be scheduled to come to the hospital for months in advance for a surgical procedure. Therefore the statistical forecast techniques may take into account both the deterministic forecasts of future flow and load as well as the statistical information such as historical forecasts or short term forecasts based on upstream patient flow. The processor of the server 150 is also capable of executing the algorithm to estimate and predict a number of individuals (e.g., patients) expected to be moved between units (e.g., general ward, ICU, etc.) and/or being discharged (e.g., allowed to go home) some time in the future for example a number of hours and/or days from a current time. It should be pointed out that length of stay estimates (LOS) are typically skew right distributions in which the mean is greater than the median. Simple small parameter curves useful for probability density function (pdf), (which is a statistical representation indicating that the length of stay in a unit is randomly distributed) estimates with these characteristics such as beta or Johnson curves may be useful in generating short term patient transition flows. For example, it may be known that a patient admitted for hip surgery has a typical LOS of three (3) days. By using this LOS information a model may be generated based on a two parameter beta curve and then if a complication occurs such as a post op fever the LOS (e.g., three days) may be modified with an adjustment of a beta parameter.

Additionally, the processor of the server is capable of executing the algorithm to generate one or more forecasts and predictions for future periods of time for example between 72 hours and 6 weeks. It should be pointed out that knowledge of current patient flow(s) in a medical institution (e.g., hospital) associated with historical based data for time frames beyond 72 hours may be utilized for generating forecasts and predictions for future periods of time between 72 hours and 6 weeks, for example.

In an exemplary embodiment, the processor of the server is capable accessing the variable input data (e.g., ADT data, etc.) and utilizing the statistical techniques of the algorithm 12, described above, and analyzing the arrival rates of individuals (e.g., patients) to a facility or a unit of a facility to determine associated time of day, day of week, and month of year variations that may be used by the processor of the server to generate forecasts and predictions regarding capacity of a facility (e.g., health care facility). For instance, the admission data of the ADT data (or any other suitable data) which is part of the variable input data may include basic arrival rates of individuals (e.g., patients) admitted to the facility or institution (e.g., hospital) or to one or more units within the facility (e.g., ED, OR, ICU, general ward, etc.) which may include data indicating the time of day, day of week and month of year that individuals were admitted to the facility. The processor of the server is capable of utilizing the algorithm to analyze this information to forecast and predict the number of individuals that will likely be admitted to the facility, or one or more units within the facility, during some time in the future.

For purposes of illustration and not of limitation, based on the variable input data, the processor of the server 150 may analyze the current census information, or any other variable input data, which may indicate the number of individuals (e.g., patients) currently admitted to a facility (e.g., hospital) and which may specify a number of individuals that are assigned to units (e.g., health care units) within the facility. The variable input data (e.g., the ADT data) may also identify current patients that are scheduled to be transferred between units of a facility, or to another health care facility or patients that are to be discharged, i.e., released from the health care facility.

Based on this information, the processor of the server may determine the current bed/room capacity of the facility and by utilizing the transfer and/or discharge information or any other variable input data, the processor of the server may forecast or predict the number of beds/rooms within the facility that will be available (i.e., unassigned) in the future for example within the next 72 hours (i.e., the next 72 hrs. ahead of a current time) or any other suitable time frame in the future. Also, the processor of the server may make determinations regarding available bed and/or room capacity on the basis of a current number of beds/rooms in use over the total number of beds/rooms available or a predicted number of beds/rooms in use over the total number of beds/rooms available.

Additionally, the processor of the server 150 may predict the number of available beds/rooms within each unit (e.g., ED, OR, ICU, etc.) of the facility in the future (e.g., within the next 72 hours) by examining scheduled patient transfer and discharge information as well as any other suitable information. Furthermore, by using the algorithm 12, the processor of the server 150 is able to determine whether the current or future bed/room availability of a unit(s) is at or near capacity (or will be at or near capacity in the future) and may determine whether the current or future bed/room availability conditions may cause a bottleneck or choke point within the unit(s). It should be pointed out that the processor of the server 150 may make the determination as to whether a unit(s) currently has a bottleneck or choke point and/or whether a unit(s) will have a future (e.g., within the next 72 hrs. or any other future time) bottleneck or choke point without departing from the spirit and scope of the invention. The bottleneck(s) or choke point(s) may indicate that there is not sufficient capacity within a unit(s) to accept additional patients.

In this regard, the processor of the server may determine that when the bed/room availability of a unit(s) within a facility is below, or predicted in the future to be below a predetermined threshold (e.g., 10% or less of the beds and/or rooms within a unit are or will be available, i.e., the unit is at least 90% full) that there is currently a bottleneck (or may be a bottleneck in the future) within the unit(s) limiting and/or prohibiting the assignment and/or placement of additional patients within the unit(s). When the processor of the server determines that there is a current (or predicts that there will be a future) bottleneck or choke point within a unit (e.g., bed/room availability in emergency room is less than 10%), the display 80 may receive a signal from the processor 80 of the server and may display the current or future bottleneck(s) or choke point(s) on the display. In this regard, a map of the facility (e.g., hospital) may be shown on the display 80 of the server illustrating one or more units that are identified by an indicator as having a bottleneck or choke point either currently or some time in the future (e.g., over the next 12 hrs., 72 hrs. or any other future time). The indicator(s) may consist of a highlighted color (e.g., red) of a visual representation within the unit(s) (e.g., medical ICU) or any other suitable indicator.

Additionally, regarding the display of bottlenecks or choke points relative to the units, the display 80 may also show a visual representation of one or more units such as health care units (e.g., ED, ICU, etc.) and an indicator, including but not limited to one or more highlighted colors that may be used to identify a certain level of congestion within the unit(s) and/or between one or more unit(s) currently or predicted to occur some time in the future. For example, a unit(s) (e.g., ED) highlighted in a color such as for example yellow may signify a low level of patient congestion determined by a predetermined threshold (e.g., 50% or more of the available beds and/or rooms of a unit are unassigned or unoccupied) which may indicate that there is currently (or will be in the future) sufficient bed/room capacity for additional patients within a unit. Similarly, a unit(s) highlighted in another color such as for example orange may signify an intermediate level of patient congestion within a unit that may be determined by a predetermined threshold (e.g., between 11% and 20% of the beds and/or rooms within a facility are currently available or will be available some time in the future) which may indicate that there is minimal bed/room availability for accepting additional patients within a unit(s). As described above, an indicator such as a unit(s) highlighted in a color red may indicate a high level of patient congestion (e.g., bottleneck or chock point) determined by a predetermined threshold (e.g., less than 10% bed/room availability) within a unit(s) and that there is currently not (or will not be some time in the future) any available bed and/or room capacity to accept any additional patients within the unit(s).

In addition, the display of the server 80 may show one or more geometrical objects (e.g., lines) connected between two or more units (e.g., between OR and ED and ED and ICU) which may indicate patient capacity in relation to the units. For instance, the processor of the server may determine or predict that the OR unit has (or will have some time in the future) a high level of patient congestion and the ED unit has an intermediate level of patient congestion, in the manner described above, such that the visual representation of the OR unit is highlighted in a color such as for example red and the visual representation of the ED unit is highlighted in a color such as for example yellow. In this regard, the processor of the server may send the display 80 a signal which allows display of a geometrical object connecting the OR and ED units. This geometrical object may include but is not limited to a line, curve or any other suitable geometrical shape or the like. The geometrical object(s) may be associated with points indicating that patients are to be scheduled for transfer from one unit (e.g., ED) to another unit (e.g., ICU). For instance, in the above example, a symbol such as for example a letter A associated with the visual representation of a unit and a line(s) may indicate that patients in a unit such as the OR are to be transferred to another unit such as the ED which may be associated with a symbol such as for example the letter B that is also associated with the line(s).

Based on the indicators (e.g., highlighted colors) of the visual representations of the unit(s), a person such as a health care representative (e.g., nurse) can determine from the display 80 of the server whether it is currently feasible (or feasible some time in the future) to transfer patients from one unit (e.g., OR) along the geometrical object (e.g., line) to another unit (e.g., ED unit) along the geometrical object (e.g., line). For instance, in the example above, the health care representative may determine from display 80 that since the OR is highlighted in red indicating a high level of patient congestion in the OR that patients may not currently be transferred to the OR due to lack of bed and/or room availability or for any other suitable reason. In this regard, personnel such as for example health care personnel may be provided with a mechanism to more effectively handle patient transfers between units resulting in fewer unnecessary patient transfers since personnel are provided with a mechanism to understand not just which beds and/or rooms are currently available, but also which beds and/or rooms will be available some time in the future (e.g., in the next 8, 12, 24, 48, 72 hours, etc.). It should be pointed out that all of the current information or future prediction information described above which is generated by the processor of the server 150 may be sent to any of the electronic devices 100, 110, 120 and 130 and these electronic devices may display this information on each of their respective displays 80 in a manner analogous to that discussed above with respect to the display of the server 150.

Referring now to FIG. 4, a display (e.g., display 80 of server 150) illustrating one or more bottlenecks or choke points in a medical institution (e.g., hospital) is provided. Additionally, FIG. 4 shows visual representations of units within the medical institution such as for example an emergency center 60, a medical unit 62, an oncology service line unit 64, a critical care unit 61, a telemetry unit 66, an OR/PACU unit 67, a surgical unit 63 and a women's center unit 68. The bottlenecks may be identified for a predetermined time period in the future. For instance, in FIG. 4 the predetermined time period is 12 hours in the future and is based on a time between 8:00 AM and 8:00 PM. While a predetermined time period of 12 hours is shown in FIG. 4, it should be pointed out that any other suitable time period may be chosen without departing from the spirit and scope of the invention. As shown in FIG. 4, the display (e.g., display 80) may indicate that the processor of the server predicts one or more patients (e.g., 3 patients) may be transferred out of a medical department (e.g., critical care unit 61) to another medical department (e.g., surgical unit 63) based on an indication that there is a bottleneck. In this regard, medical personnel of a medical institution may utilize the information on the display to facilitate the transfer of one or more patients (e.g., 3 patients) from one medical department(s) (e.g., critical care unit 61) to another medical department(s) (e.g., surgical unit 63).

In FIG. 4, a prediction of a very high level of congestion and bottlenecks 5 may be identified by a colored bar such as for example a red bar. It should also be pointed out that any other suitable color may be used to identify a bottleneck within a medical unit without departing from the spirit and scope of the invention. Additionally, one or more bottlenecks within medical units of one or more medical facilities may also be shown in the display. For instance, as shown in FIG. 4, the medical intensive care unit (ICU) and the neuro ICU, of the critical care facility, each indicate that there are predicted to be bottlenecks 5 within these the medical ICU and neuro units. It should also be pointed out that an orange bar 71 (or any other suitable colored bar) may be used to signify a prediction of a still somewhat high level of patient congestion determined by a predetermined threshold (e.g., 80% or more of the available beds and/or rooms of a unit are assigned or occupied) which may indicate there is currently (or will be in the future) insufficient bed/room capacity for additional patients within a unit. Moreover yellow bar 70 (or any other suitable colored bar) may signify a prediction of an intermediate level of patient congestion within a unit (emergency center 60) that may be determined by a predetermined threshold (e.g., between 80% and 60%) which may indicate that there will be minimal bed/room availability for accepting new patients within a unit(s). A green bar 73 (or any other suitable colored bar) may be used to signify that there is predicted to be no patient congestion in a portion of a unit (e.g., oncology service line unit 64), which may indicate there will be sufficient bed/room capacity for additional patients within a unit.

Referring now to FIG. 5, a display illustrating predicted patient flow within a unit of a medical institution is provided. The display (e.g., display 80) of FIG. 5 may illustrate predicted patient capacity and may specify one or more predictions for a predetermined time frame in the future, in this example 12 hours in the future. All of the predictions shown in FIG. 5 may be generated by the processor of the server 150 upon executing the algorithm 12 and may be sent by the processor to a display(s). The predictions may be generated for a time period between 8:00 AM to 8:00 PM of a given day, or any other suitable time period. As illustrated in FIG. 5, eight patients 2 are predicted to be come into this unit from various other locations, for example. In this regard, the display may indicate that a patient 8 is predicted to enter the unit between the hours of 2:00 PM and 3:00 PM from the emergency center 1 and may indicate that a patient 10 is predicted to enter the unit between the hours 6:00 PM and 7:00 PM from the emergency center. Additionally, the display of FIG. 5 may indicate that two patients 4 and 6 are predicted or forecasted to transfer into the unit. In this regard, the display may indicate that a patient 4 has transferred into the unit and that the patient's 4 stay within the medical institution (e.g., hospital) has currently been extended beyond an initially planed stay and is now overdue. Also, the display may indicate that a patient 6 with special needs is predicted to enter the unit (or occupy a room) between the hours of 3:00 PM and 4:00 PM.

Additionally, the display of FIG. 5 may indicate that 4 patients were previously scheduled to be admitted to a medical unit. All of the data shown in FIG. 5 may be generated by the processor of the server 150 upon executing the algorithm 12 and may be sent by the processor to a display(s). In this regard, the display may indicate that patient 11 has special needs and is scheduled to occupy a room between the hours of 8:00 AM and 9:00 AM and that patient 12 has special needs and is scheduled to occupy a room between 10:40 AM and 11:05 AM, for example. Moreover, the display may indicate that patient 14 is predicted to be assigned a bed between the hours of 12:00 PM and 1:00 PM and that patient 15 is predicted to be assigned a bed between the hours of 5:00 PM and 6:00 PM.

The display of FIG. 5 may also illustrate patients 9 that are to be released from the medical unit via transfers to other medical departments or by being discharged from the medical institution (e.g., hospital). For instance, between the hours of 8:00 AM and 9:00 PM a patient 16 may be scheduled or predicted to be transferred from the medical department to another medical department within the medical institution (e.g., hospital). Similarly, a patient 17 may be scheduled or predicted to be transferred from the medical department to another medical department within the medical institution between the hours of 6:00 PM and 7:00 PM. FIG. 5 also illustrates that 4 patients may be scheduled for discharge from the medical department. For instance, patient 18 may be currently scheduled or predicted to be discharged between the hours of 9:00 AM and 10:00 PM. This discharge may be confirmed as ready to indicate that all administrative procedures (e.g., completion of appropriate forms, etc.) have been met for the patients' 18 discharge from the medical department. Additionally, patient 19 may be scheduled or predicted to be discharged from the medical department between the hours of 11:00 AM and 12:00 PM and this discharge may be confirmed as ready to indicate that all administrative procedures have been met for the patient's discharge as well. Furthermore, the display may indicate that patient 20 is scheduled or predicted to be discharged from the medical department between the hours of 3:00 PM and 4:00 PM and that patient 21 is scheduled or predicted to be discharged from the medical department between the hours of 5:00 PM and 6:00 PM. The discharges associated with patients 20 and 21 may not be confirmed as ready indicating that additional administrative procedures (e.g., completion of appropriate forms, etc.) should be completed before patients 20 and 21 are allowed to be discharged from the medical department.

Referring now to FIG. 6, a display illustrating medical information associated with one or more patients is provided. As shown, in FIG. 6, a display such as for example display 80 may indicate the status of a patient as inbound (IN) signifying that a patient(s) is predicted to be admitted to a medical department or may indicate the status of a patient as outbound (OUT) signifying that the patient(s) is scheduled or predicted to be released from a medical department. Additionally, the display may indicate a room number (e.g., 762) that a patient (e.g., Elizabeth Murr) is assigned to occupy and may specify the patient's age (e.g., 41), sex (e.g., Female (F)), diagnosis (e.g., MVA) and a location of the unit in which the patient is located (e.g., emergency center (EC). Additionally, the display of FIG. 6 may indicate a typical discharge (DC) time (e.g., 03/06/08 at 11:00 AM) as well as a forecasted or predicted discharge time (e.g., 03/04/08 at 10:00 AM). By viewing the display shown in FIG. 6, medical staff of a medical institution can easily identify relevant medical data associated with one more patients such as easily identifying the patient's location within the medical institution as well as plan for forecasted discharges of the patient(s) from the medical institution.

Referring now to FIG. 7, a display showing one or more short term predictions associated with medical personnel of a medical institution (e.g., hospital), is provided. It should be pointed out that the short term predictions may be generated by the processor of the server 150 upon execution of the algorithm 12 and data associated with the predictions may be provided by the processor to a display such as the display (e.g., display 80) of FIG. 7. The short term predictions may be generated for a term such as 12 hours (e.g., 7 am-7 pm) for a given day (e.g., 08/22/08) or any other suitable time periods in the future (e.g., 3 to 72 hours in the future). In FIG. 7, a historical data curve 25 associated with historical data regarding a number of patients that are typically (or historically) within a medical unit (e.g., an Orthopedic unit (i.e., also referred to herein as Ortho)) of a medical institution during specified times of a given day of the week is shown. For instance, the historical data curve 25 indicates that historically there are 10 patients within the Ortho unit requiring medical attention at 1:00 PM on a given day of the year (e.g., August 22nd). Additionally, a predicted data curve 27 associated with a forecast or prediction regarding a number of patients that are expected to be within the Ortho unit at specified times during a given day of the week is shown in FIG. 7. For example, the predicted data curve 27 indicates that 27 patients are predicted to be within the Ortho unit requiring medical attention at 1:00 PM of a given day of the year (e.g., Aug. 22, 2008).

Additionally, the display of FIG. 7 may show that the number of medical staff that are currently scheduled to work over specified time periods of a given day in order to provide adequate medical attention to patients. For instance, the display may show that 5 registered nurses (RNs), 5 licensed practical nurses (LPNs) and 7 certified nursing assistants (CNAs) are currently scheduled to work during a time. Furthermore, the display may show types of resources 23 that are currently allocated during specified times of a given day. In this regard, for example, the display may show that for the date of Aug. 22, 2008, the Ortho unit there has a bed capacity of 28 beds and may indicate that 5 RNs, 5 LPNs and 7 CNAs are scheduled to work during a time period between 7:00 AM to 3:00 PM. It should be pointed out that the display may show that the processor of the server 150, upon executing the algorithm 12, predicted (See e.g., element 28 of FIG. 7) that 12 patients (See e.g., element 29 of FIG. 7) are expected to be transferred into the Ortho unit from one more other units at a specified time of the day (e.g., 1:00 PM on Aug. 22, 2008). In this regard, the processor of the server may generate one or more recommendations (See e.g., elements 22 and 24 of FIG. 7). For instance, the processor of the server may generate a recommendation 22 that an increase of one RN and one CNA is needed to work during a time frame (e.g., 7:00 AM to 3:00 PM) in order to accommodate a number of predicted patient transfers (e.g., 12 patient transfers) within the medical unit (e.g., Ortho unit) to occur at a specified time (e.g., 1:00 PM) and data associated with this recommendation may be shown on the display of FIG. 7.

The display of FIG. 7 may also show predicted patient per nurse curve 26, a historical patient per nurse curve 30, as well as a target patient per nurse 32 line, a minimum patient per nurse line 34 and a maximum patient per nurse line 36. For example, the predicted patient nurse curve 26 shows a predicted number of patients per nurse during various times of a day and the historical patient per nurse curve 30 shows a historical number of patients per nurse during various times of a day. In this regard, the display may show that the processor of the server predicted that the nurse to patient ratio target should be 5 patients to 1 nurse at a specified time such as 1:00 PM on a given day of the year (e.g., Aug. 22, 2008). (See e.g., predicted patient per nurse curve 26) Also, the display may show that historically the nurse to patient ratio is typically around 3 patients to 1 nurse at a specified time (e.g., 1:00 PM) of a given day of the year (e.g., Aug. 22, 2008). (See e.g., historical patient per nurse curve 30) The target nurse to patient ratio line 32 may also show that the processor of the server determined the target nurse to patient ratio during various times of a day. For instance, the display may show that at 1:00 PM on Aug. 22, 2008 a target number of patients per nurse is 4. (See e.g., target patient per nurse line 32) Additionally, the minimum patient per nurse line 34 may show a projected minimum number of patients that should be assigned to a nurse during specified times of a day whereas the maximum patient per nurse line 36 may show a maximum number of patients that should be assigned to a nurse during various times of a day. In this regard, for example, the display may show that at 1:00 PM on Aug. 22, 2008 a minimum number of patients per nurse that may be assigned to a nurse is 4 whereas a maximum number of patients per nurse at 1:00 PM on Aug. 22, 2008 is 6. (See e.g., minimum patient per nurse line 34 and maximum patient per nurse line 36)

Referring now to FIG. 8, a display showing one or more medium term predictions associated with medical personnel of a medical institution (e.g., hospital), is provided. It should be pointed out that the medium term predictions may be generated by the processor of the server 150 upon execution of the algorithm 12 and data associated with the predictions may be provided by the processor to a display such as the display (e.g., display 80) of FIG. 8. The medium term predictions may be generated for a time in the future, such as for example 4 weeks in the future or any other suitable time periods in the future (e.g., 4 weeks to 8 weeks in the future). For instance, on a given date, i.e., Jul. 25, 2008, the processor of the server may be utilized to generate one or more medium term predictions for a given date 4 weeks in the future such as for example Aug. 22, 2008. The predications shown in FIG. 8, that are generated by the processor of the server, may be related to a time period (e.g., 12 hours, i.e., 7 am-7 pm)) on a given day (e.g., Aug. 22, 2008) in the future. FIG. 8 shows historical data curves and predicted data curves associated with predictions for various units such as an Ortho unit, a Telemetry unit, an ICU and a Cardiac ICU. In particular, FIG. 8 shows a predicted data curve 40 and a historical data curve 42 associated with the Ortho unit, a predicted data curve 41 and a historical data curve 43 corresponding to the Telemetry unit, a predicted data curve 44 and a historical data curve 46 corresponding to the ICU as well as a predicted data curve 45 and a historical data curve 47 corresponding to a Cardiac ICU. Each of the predictive data curves 40, 41, 44 and 45 show a predicted number of patients that is expected to be within a respective unit (e.g., Ortho unit) during various times throughout the day. For instance, during a given time period, such as for example, between the hours of 1:00 PM and 2:00 PM on a given day (e.g., Aug. 22, 2008), the predicated data curve may indicate that 20 to 25 patients are expected to be within the Ortho unit. On the other hand, the historical data curve 42 shows that between the hours of 1:00 PM and 2:00 PM on a given day (e.g., Aug. 22, 2008), the number of patients that are historically within Ortho unit ranges between 9 to 10.5.

The display of FIG. 8 may also show one or more recommendations as to the number of medical staff personnel that are suggested to be scheduled to work during one or more particular time periods based on the predicted number of patients that are expected to be within a medical unit during a respective time period. The predicted number of patients within the medical unit during various times of a day may be identified by the predicted data curves as described above. As an example of the display of FIG. 8 illustrating a recommended number of medical staff based on prediction data, consider the predictive data curve 44 associated with the ICU. During the hours of 7:00 AM to 3:00 PM on a given day (e.g., Aug. 22, 2008), the processor of the server may utilize the prediction data associated with the prediction data curve 44 and recommend that 5 RNs, 5 LPNs and 7 CNAs should be scheduled to work from 7:00 AM to 3:00 PM in order to provide adequate medical care for patients and these medical staff recommendations are shown on the display of FIG. 8. The processor of the server may also utilize the prediction data associated with the prediction data curve 44, corresponding to a time period between 4:00 PM and 7:00 PM, and recommend that 3 LPNs and 4 CNAs should be scheduled to work from 4:00 PM to 7:00 PM on a given day (e.g., Aug. 22, 2008) in order to provide adequate medical care for predicted patients and these medical staff recommendations are also shown on the display of FIG. 8.

It should be pointed out that since the predicted number of patients, as indicated by the predicted data curve 44, was less during the time frame between 4:00 PM and 7:00 PM as opposed to the time frame between 7:00 AM and 3:00 PM, the processor of the server recommended a lower amount of medical staff (e.g., 3 LPNs, 7 CNAs) to work during the 4:00 PM to 7:00 PM time frame versus the recommended number of medical staff during the 7:00 AM to 3:00 PM time frame (e.g., 5 RNs, 5 LPNs, 7 CNAs). The highlighted bands on a specific time period, such as for example, the highlighted time at 1:00 PM associated with the Ortho unit as well as the highlighted time at 10:00 PM (highlighted in yellow) associated with the ICU and the highlighted time at 6:00 PM associated with the Cardiac ICU may signify a mechanism of alerting a user to a potential problem at during the time period and indicate that the user should evaluate one or more conditions or resources (e.g., understaffing, overstaffing, census at capacity, etc.).

As described above, the exemplary embodiments may use historical data to determine or predict future capacity and resource needs of a facility. For instance, based on the variable input data, the processor of the server 150 is capable of analyzing historical data associated with a given time or during a given time period such as for example a given month (e.g., December). In this regard, for example, the processor of the server 150 may determine that for the past 5 years, 200 individuals (e.g., patients) were admitted to a facility such as a hospital and that of those individuals, 50% (i.e., 100 individuals) were admitted to a unit such as the emergency department, while 20% (i.e., 40 individuals) were admitted to the operating room, 20% (i.e., 40 individuals) were admitted to the ICU and 10% (i.e., 20 individuals) were admitted to the general ward. Based on this information, the processor of the server 150 may utilize the statistical techniques of the algorithm 12 to predict and forecast the amount of beds and/or rooms that will likely need to be available during a given time of day, day of week, and month of year, which in this example is December. In this regard, the processor of the server 150 is also capable of analyzing historical data, census data, currently existing schedule data associated with one or more schedules identifying work times of staff personnel, or any other suitable data of the variable input data 3 to determine and predict a number of staff members (e.g., doctors, nurses, etc.) that would likely need to be scheduled to work in the future in order to fulfill demand needs and provide appropriate care for patients. In this example, the processor of the server 150 may predict future staff needs and recommend staff schedules for a given time in the future such as the month of December for an upcoming year. However, the predicted staff needs and staff schedules may be determined for any other suitable time in the future (e.g., within the next 72 hrs.)

As described above, the processor of the server 150 may evaluate historical data, census data and currently existing schedule data of the variable input data 3 to determine that a certain amount of staff personnel will need to work in order to address patient needs. The processor of the server 150 may also utilize this data to determine the number of staff that should be scheduled to work in one or more units of a facility some time in the future. In this regard, the processor of the server 150 may analyze the historical data to determine the average number of staff personnel that worked within each unit of a facility during a given time period (e.g., the month of December) and the processor of the server 150 may use the average as the number of staff required to work in respective units within the facility for some time in the future (e.g., December of the upcoming year). For example, the processor of the server 150 may determine or predict that 10 nurses and 3 physicians should be scheduled to work in the emergency department unit for a given time in the future such as for a given day or a given week in the month of December in order to handle predicted patient needs (i.e., to cover the needs of 100 patients in the ED in the e.g., above). Similarly, the processor of the server 150 may determine or predict that 7 nurses and 2 physicians need to be assigned and scheduled to work in the operating room unit to address predicted patient needs for a given day or week in the month of December (i.e., to cover the needs of 40 patients in the OR in the e.g., above).

In an alternative exemplary embodiment, one or more rules may be generated defining one or more predetermined ratios of predicted patients relative to staff personnel for units within a facility. These rules may but need not be generated by a person utilizing the user input interface 82 of the server to define the rules which may be stored in the memory 86 of the server 150. These predetermined ratios may be based on historical data associated with the average patient to staff ratio within a unit during a given time in the past (e.g., December of a previous year). In this regard, the processor of the server 150 may predict the number of staff personnel scheduled to work in the future for a given unit based on a defined predetermined ratio of predicted patients relative to staff personnel (e.g., 10 patients to 2 staff personnel members or any other suitable ratio) for a given unit. It should be pointed out that each unit may, but need not be, defined to have a different ratio depending on patient demand variations within units of the facility for a given time period. For instance, the patients in the ICU unit may require a higher level of care during a given time than the patients in the Ortho Unit and as such the ratio of patients to staff for the ICU unit may be defined to be higher than the ratio for the Ortho Unit, for example.

Additionally, the processor of the server 150 is capable of adjusting recommended scheduling needs when the processor receives real-time information indicating that there is a change in a schedule such as for example one or more staff members (e.g., nurses, physicians, etc.) taking a work day off, calling in sick or one or more patients canceling an appointment, not showing for a scheduled event such as surgery or for any other reasons. When these changes are made whether in real time or some time in the future, the processor of the server 150 may automatically adjust the predictions and recommend alternative personnel to the schedule(s) to fill in for previously scheduled staff personnel (who are no longer available) some time in the future (e.g., over the next 72 hrs. or any other time in the future). Additionally, the processor of the server 150 may recommend that staff personnel be reduced when demand no longer dictates that the personnel are needed at a given time in the future such as, for example, when a patient cancels a scheduled appointment for surgery, or for any number of other reasons. It should be pointed out that all of the prediction information associated with scheduling and staff needs, etc. may be shown on the display of the server 150 and this information may be sent to any of the other electronic devices 100, 110, 120, and 130 shown on the displays of these electronic devices.

Referring now to FIG. 9, a display showing one or more predictions associated with scheduling medical staff personnel is provided. It should be pointed out that the scheduling data may be generated by the processor of the server 150 upon execution of the algorithm 12 and the scheduling data may be provided by the processor to a display such as the display (e.g., display 80) of FIG. 9. The scheduling data may be generated for a time in the future, such as for example 30 days in the future or any other suitable time periods. For instance, in the exemplary embodiment of FIG. 6, the scheduling data predictions may be generated for 30 days, such as for example, August 16, August 17, August 18, August 19, August 20, August 21, August 22, August 23, August 24, August 25, August 26, August 27 and August $28^{th}$ of a given year. The display of FIG. 9 illustrates a predicted data curve 48 and a historical data curve 50. The historical data curve 50 indicates a number of patients that are historically within, or admitted to, a medical unit during various dates of the year (e.g., August $16^{th}$ to August $27^{th}$). For instance, the historical data curve 50 indicates that on August $17^{th}$ of a given year, a number of patients that historically are within, or admitted to, the medical unit is 5. The predicted data curve 48 indicates a number of patients that are expected or predicted to be within, or admitted to, a medical unit during various dates of the year (e.g., August $16^{th}$ to August $27^{th}$). For example, the predicted data curve 48 indicates that on August $17^{th}$ of a given year (e.g., 2008) that a predicted number of patients is expected to be within, or admitted to, the medical unit is 11.

It should be pointed out that the processor of the server may generate a recommended schedule (e.g., "Schedule 1") associated with a recommended allocation of one or more types of resources (e.g., resource type 57) which may be shown on the display (e.g., display 80). For instance, a recommendation associated with resource type 57 may specify that there is a bed capacity of 28 beds in a medical unit, and may indicate that 5 RNs, 5 LPNs and 7 CNAs are recommended to work during particular days to provide adequate medical care to handle the predicted number of patients in that unit.

The display of FIG. 9, may also show a predicted patient per nurse curve 51 (also referred to herein as a nursing hours per patient day (NHPPD) curve), a historical patient per nurse curve 49, as well as a target patient per nurse line 52, a minimum patient per nurse line 53 and a maximum patient per nurse line 55. The predicted patient per nurse curve 51 shows a predicted nurse to patient ratio for one or more days and the historical patient per nurse curve 49 shows a historical number or patients per nurse corresponding to various days. For instance, on a given day such as August 23$^{rd}$ the predicted patient per nurse curve 51 indicates that processor of the server determined that the nurse to patient ratio should be 6 patients to 1 nurse based on the predicted census for that unit whereas the historical patient per nurse curve 49 indicates for August 23$^{rd}$ that the nurse to patient ratio has been 5 patients to 1 nurse. Also, the target patient per nurse line 52 may also show that the processor of the server determined a target number of patients per nurse corresponding to one or more days of the year. For instance, the target patient per nurse line 52 may show that on a given day such as August 23$^{rd}$, a recommended target nurse to patient ratio is 5.5 patients to 1 nurse.

The minimum patient per nurse line 53 may show a recommendation as to the minimum number of patients that may be assigned to each nurse during one or more days (e.g., 08/16 through 08/27) whereas the maximum patient per nurse line 55 may show a recommendation as to the maximum number of patients per nurse that may be assigned to each nurse during one or more days (e.g., 08/16 through 08/27). In this regard, for example, the display may show that on August 23$^{rd}$ a minimum number of patients per nurse recommended to be assigned to each nurse is of 4.9 whereas on August 23$^{rd}$ a maximum number of patients per nurse recommended to be assigned to each nurse is 6.5.

Additionally, it should be pointed out that the exemplary embodiments also allow users to utilize the user input interface 82 of the server 150 to alter variables of the variable input data, including but not limited to information relating to census, staffing, admission(s), discharge(s), and transfer(s) data so that the processor of the server 150 may provide a number of possible scenarios that may be utilized to determine the outcome and impact on potential scheduling and staffing options prior to these schedule(s) and staffing options being accepted by the user(s) for implementation by a facility.

Referring now to FIG. 10, a flowchart for illustrating a mechanism of utilizing variable input data to generate one or more current and future conditions regarding capacity and/or resources in a facility or institution is provided. At operation 1000, the processor of a device such as a server 150 may analyze some or all of the variable input data. At operation 1010, the processor of the server may execute an algorithm such as algorithm 12 and determine or predict current and/or future conditions associated with capacity and/or resources of a facility such as for example a heath care facility (e.g., hospital). For instance, as described above, the processor of the server may determine the number of available beds and/or rooms within the facility and within one or more units of the facility. Data associated with the number of available beds and/or rooms may be shown on a display of a server and may be sent to electronic devices such as electronic devices 100, 110, 120 and 130 which may also show this information on their displays. At operation 1020, the processor of the server may determine which units of a facility or institution may currently be at or near capacity and which may be at or near capacity in the future. For instance, the processor of the server 150 may determine a level of congestion (e.g., low level, intermediate level and high level of congestion) associated with each unit within the facility in a manner analogous to that discussed above.

At operation 1030, the server of the processor may determine whether there currently is a bottleneck(s) or choke point(s) within a unit(s) (e.g., OR, ED, ICU, general ward, etc.) and/or between units of a facility and the processor of the server may predict whether there will likely be a bottleneck(s) or choke point(s) within a unit(s) and/or between units of a facility some time in the future (e.g., within the next 8, 12, 24, 48, 72 hrs., etc.). These bottlenecks or choke points may be shown on a display of a server and/or on a display of electronic devices such as electronic devices 100, 110, 120 and 130. At operation 1040, the processor of the server 150 may automatically determine current and future staffing needs and generate current and/or future recommendations regarding scheduling and staffing in a manner analogous to that discussed above. Optionally, at operation 1050, the processor of the server 150 may determine whether there are individuals (e.g., patients) that can be discharged from a facility (e.g., hospital) prior to a scheduled discharge time or transferred to another unit(s). In this regard, the processor of the server is capable of recommending the acceleration of the discharge and transfer of patients admitted to a facility. For instance, personnel of the facility may utilize the user input interface 82 of the server to update patient information to indicate that a patient's medical/health status is great and the processor of the server may analyze this updated patient information (or any other suitable information) and determine that a patient may be discharged (e.g., allowed to return home) prior to a scheduled or anticipated discharge time. This may open up space such as beds and/or rooms within units so that the facility can accept new patients and generate new revenue. Similarly, based on the updated patient information (e.g., information indicating that the patient is healthy) or any other suitable information, the processor of the server 150 may determine that a patient(s) should be transferred from one unit to a less expensive unit. Transfer of patients from expensive units to less expensive units also results in increased efficiency of resources in a health care facility such as a hospital since it is often the case that hospitals lose money on patients staying in expensive ICU or critical care units (CCU) but often make a profit when patients do not spend time in the these units or spend time in other units.

Optionally, at operation 1060, the processor of the server may recommend the addition or removal of staff personnel and/or other individuals (e.g., patients) from schedules for current and future time periods based on predicted demand changes of a facility, assigned staff being unable to work a scheduled time, patients missing scheduled appointments or for any other number of reasons. Optionally, at operation 470, the processor of the server may recommend adjustments to scheduled admission information. For instance, the processor of the server 150 may recommend adjustments to scheduled patient admission information on the basis of one or more patient cancellations, early discharges, transfers between units within a facility or for any other suitable number of reasons. After operation 1070, the process may end or the process in operations 400-470 may be repeated. For instance, if the processor of the server 150 determines that there are additional predictions and/or current conditions that need to be evaluated regarding the capacity and allocation of resources within a facility, then the process in operations 400-470 may be repeated. Otherwise, the process may end.

It should be understood that each block or step of the flowchart shown in FIG. 4 and combination of blocks in the flowchart, can be implemented by various means, such as hardware, firmware, and/or software including one or more computer program instructions. For example, one or more of the procedures described above may be embodied by computer program instructions. In this regard, the computer program instructions which embody the procedures described above may be stored by a memory device of the server and/or the electronic devices and executed by a processor in the electronic device and/or the network entities, e.g., server. As will be appreciated, any such computer program instructions may be loaded onto a computer or other programmable apparatus (i.e., hardware) to produce a machine, such that the instructions which execute on the computer or other programmable apparatus (e.g., hardware) means for implementing the functions implemented specified in the flowcharts block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the functions specified in the flowcharts block(s) or step(s). The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions that are carried out in the system.

The above described functions may be carried out in many ways. For example, any suitable means for carrying out each of the functions described above may be employed to carry out the invention. In one embodiment, all or a portion of the elements of the invention generally operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

By utilizing the exemplary embodiments of the invention, a mechanism is provided in which to manage the flow of individuals (e.g., patients) within a facility such as a health care facility (e.g., hospital) and which enables staff to easily understand the current and future bottlenecks or choke points that may occur within and between units in the facility which may affect patient flow. In this regard, the exemplary embodiments provide visibility and identification of current and potential future risks to patient flow within a facility and may highlight current and predict excessive demand between units within a facility so that staff personnel are better able to plan for future needs and allocate appropriate resources.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method comprising:
   analyzing data comprising information associated with a health care entity, said data comprising clinical data associated with one or more patients currently within the health care entity, wherein at least some of the data is generated in real-time during an actual time in which one or more events occur;
   using at least a portion of the data to generate one or more predictions regarding one or more conditions to occur in the future that are associated with one or more resources of the entity;
   analyzing, via a processor, one or more results of the predictions and recommending an allocation of at least one of the one or more resources on the basis of the results;
   determining that one of the one or more conditions corresponds to a number of patient transfers and a number of patient discharges during a predetermined time period in the future;
   determining that another of the conditions corresponds to a number of beds or rooms in one or more units of the entity that will be available at a predetermined time or during a predetermined time period in the future;
   determining that another of the conditions corresponds to one or more levels of congestion within one or more units of the entity, the congestion corresponds to a number of patients assigned to a respective unit, the levels of congestion being determined based in part on a comparison of at least a subset of the number of the beds or rooms that are determined as unoccupied by a patient to a predetermined threshold signifying a level of patient congestion for the respective unit;
   determining that the respective unit is congested with patients in an instance in which the number of the beds or the rooms that are determined as unoccupied is below the predetermined threshold;
   utilizing at least one of the levels of congestion to determine whether to assign one or more other patients to another respective unit of the entity; and
   generating at least one recommendation of a number of persons to schedule for providing medical care for a time period in the future for the patients in at least one of the units based in part on a prediction of a number of patients expected to occupy the unit during the time period in the future, wherein the number of persons to schedule and the prediction of the number of patients is determined based in part on analyzing historical data indicating an average patient to medical personnel ratio within the unit during a corresponding time period in the past.

2. The method of claim 1, further comprising using the portion of the data to determine one or more future conditions associated with the one or more resources.

3. The method of claim 1, wherein identifying comprises determining a number of beds or rooms predicted to be in use at the predetermined time or during the predetermined time period.

4. The method of claim 3, wherein the one or more units comprise one or more health care units.

5. The method of claim 1, wherein one of the conditions corresponds to one or more levels of congestion relative to at least two units of the entity, the congestion corresponds to a number of individuals assigned to a respective unit, and wherein the method further comprises utilizing at least one of the levels of congestion to determine whether to transfer one or more other individuals from a first unit to a second unit among the two units.

6. The method of claim 5, further comprising:
   displaying the congestion relative to the at least two units; and
   utilizing one or more indicators that correspond to the one or more levels of congestion and which are associated with visual representations of the at least two units to determine whether to transfer the other individuals from the first unit to the second unit.

7. The method of claim 1, wherein at least one of the predictions comprises predicting the number of persons scheduled which are needed to work within the at least one unit of the entity for the time period in the future; and
   recommend adding or removing one or more identifiers associated with the persons from one or more staff schedules based on at least one of the results of the predictions, the schedules comprise data indicating the time period in the future that events are designated to occur.

8. The method of claim 7, further comprising identifying circumstances causing recommendations for changes to the one or more staff schedules and recommending a modification to the one or more staff schedules before the time in the future.

9. The method of claim 1, wherein the clinical data comprises one or more orders, acuity information or diagnosis information associated with the patient.

10. An apparatus comprising:
at least one processor and at least one memory storing computer code, which when executed by the processor causes the apparatus to:
analyze data comprising information associated with a health care entity, said data comprising clinical data associated with one or more patients currently within the health care entity, wherein at least some of the data is generated in real-time during an actual time in which one or more events occur;
use at least a portion of the data to generate one or more predictions regarding one or more conditions to occur in the future that are associated with one or more resources of the entity;
analyze one or more results of the predictions and recommend an allocation of at least one of the one or more resources on the basis of the results;
determine that one of the one or more conditions corresponds to a number of patient transfers and a number of patient discharges during a predetermined time period in the future;
determine that another of the conditions corresponds to a number of beds or rooms in one or more units of the entity that will be available at a predetermined time or during a predetermined time period in the future;
determine that another of the conditions corresponds to one or more levels of congestion within one or more units of the entity, the congestion corresponds to a number of patients assigned to a respective unit, the levels of congestion being determined based in part on a comparison of at least a subset of the number of the beds or rooms that are determined as unoccupied by a patient to a predetermined threshold signifying a level of patient congestion for the respective unit;
determine that the respective unit is congested with patients in an instance in which the number of the beds or the rooms that are determined as unoccupied is below the predetermined threshold;
utilize at least one of the levels of congestion to predict whether to assign one or more other patients to another respective unit of the entity; and
generate at least one recommendation of a number of persons to schedule for providing medical care for a time period in the future for the patients in at least one of the units based in part on a prediction of a number of patients expected to occupy the unit during the time period in the future, wherein the number of persons to schedule and the prediction of the number of patients is determined based in part on analyzing historical data indicating an average patient to medical personnel ratio within the unit during a corresponding time period in the past.

11. The apparatus of claim 10, wherein when the processor executes the computer code, the apparatus is further configured to use the portion of the data to determine one or more future conditions associated with the one or more resources.

12. The apparatus of claim 10, wherein when the processor executes the computer code, the apparatus is further configured to identify the number by determining a number of beds or rooms predicted to be in use at the predetermined time or during the predetermined time period in the future.

13. The apparatus of claim 10, wherein the one or more units comprise one or more health care units.

14. The apparatus of claim 10, wherein when the processor executes the computer code, the apparatus is further configured to:
determine, in the future, that one of the conditions corresponds to one or more levels of congestion relative to at least two units of the entity, the congestion corresponds to a number of individuals assigned to a respective unit; and
utilize at least one of the levels of congestion to determine whether to transfer one or more other individuals from a first unit to a second unit among the two units.

15. The apparatus of claim 14, wherein when the processor executes the computer code, the apparatus is further configured to:
display the current and future congestion relative to the at least two units and
utilize one or more indicators that correspond to the one or more levels of congestion and which are associated with visual representations of the at least two units to determine whether to transfer the other individuals from the first unit to the second unit.

16. The apparatus of claim 10, wherein when the processor executes the computer code, the apparatus is further configured to:
determine that at least one of the predictions comprises predicting the number of persons scheduled which are needed to work within the at least one unit of the entity for the time period in the future; and
recommend adding or removing one or more identifiers associated with the persons from one or more staff schedules based on at least one of the results of the predicting, the schedules comprise data indicating the time period in the future that events are designated to occur.

17. The apparatus of claim 16, wherein when the processor executes the computer code, the apparatus is further configured to:
identify circumstances causing recommendations for changes to the one or more schedules; and
recommend a modification of the one or more staff schedules before the time in the future.

18. A computer program product, the computer program product comprising at least one non-transitory computer-readable storage medium having computer-readable program code portions stored therein, the computer-readable program code portions comprising:
a first executable portion for analyzing data, comprising information associated with an entity, said data comprising clinical data associated with one or more patients currently within the health care entity, wherein at least some of the data is generated in real-time during an actual time in which one or more events occur;
a second executable portion for using at least a portion of the data to generate one or more predictions regarding one or more conditions to occur in the future that are associated with one or more resources of the entity;
a third executable portion for analyzing one or more results of the predictions and recommending an allocation of one or more resources on the basis of the results;

a fourth executable portion for determining that one of the one or more conditions corresponds to a number of patient transfers and a number of patient discharges during a predetermined time period in the future;

a fifth executable portion for determining that another of the conditions corresponds to a number of beds or rooms in one or more units of the entity that will be available at a predetermined time or during a predetermined time period in the future;

a sixth executable portion for determining that another of the conditions corresponds to one or more levels of congestion within one or more units of the entity, the congestion corresponds to a number of patients assigned to a respective unit, the levels of congestion being determined based in part on a comparison of at least a subset of the number of the beds or rooms that are determined as unoccupied by a patient to a predetermined threshold signifying a level of patient congestion for the respective unit;

a seventh executable portion for determining that the respective unit is congested with patients in an instance in which the number of beds or the rooms that are determined as unoccupied is below the predetermined threshold;

an eighth executable portion for utilizing at least one of the levels of congestion to predict whether to assign one or more other patients to another respective unit of the entity; and a ninth executable portion for generating at least one recommendation of a number of persons to schedule for providing medical care for a time period in the future for the patients in at least one of the units based in part on a prediction of a number of patients expected to occupy the unit during the time period in the future, wherein the number of persons to schedule and the prediction of the number of patients is determined based in part on analyzing historical data indicating an average patient to medical personnel ratio within the unit during a corresponding time period in the past.

19. The computer program product of claim 18, wherein utilizing comprises utilizing the level of congestion to determine whether to recommend assigning the one or more other individuals to the respective unit to meet future patient demand.

20. The computer program product of claim 18, further comprising a tenth executable portion for using the portion of the data to determine one or more current and future conditions associated with the one or more resources.

21. The computer program product of claim 18, wherein identifying comprises determining a number of beds or rooms predicted to be in use at the predetermined time or during the predetermined time period.

22. The computer program product of claim 18, wherein one of the conditions corresponds to one or more current and future levels of congestion relative to at least two units of the entity, the congestion corresponds to a number of individuals assigned to a respective unit, and wherein the computer program product further comprises a tenth executable portion for utilizing at least one of the levels of congestion to determine whether to transfer one or more other individuals from a first unit to a second unit among the two units.

23. The computer program product of claim 22, further comprising:
  an eleventh executable portion for displaying the congestion relative to the at least two units; and
  a twelfth executable portion for utilizing one or more indicators that correspond to the one or more levels of congestion and which are associated with visual representations of the at least two units to determine whether to transfer the other individuals from the first unit to the second unit.

* * * * *